(12) United States Patent
Zhou et al.

(10) Patent No.: US 7,751,528 B2
(45) Date of Patent: Jul. 6, 2010

(54) STATIONARY X-RAY DIGITAL BREAST TOMOSYNTHESIS SYSTEMS AND RELATED METHODS

(75) Inventors: Otto Z. Zhou, Chapel Hill, NC (US); Guang Yang, Minneapolis, MN (US); Jianping Lu, Chapel Hill, NC (US); David Lalush, Cary, NC (US)

(73) Assignees: The University of North Carolina, Chapel Hill, NC (US); North Carolina State University, Raleigh, NC (US)

( * ) Notice: Subject to any disclaimer, the term of this patent is extended or adjusted under 35 U.S.C. 154(b) by 0 days.

(21) Appl. No.: 12/176,056

(22) Filed: Jul. 18, 2008

(65) Prior Publication Data

US 2009/0022264 A1 Jan. 22, 2009

Related U.S. Application Data

(60) Provisional application No. 60/961,175, filed on Jul. 19, 2007.

(51) Int. Cl.
*A61B 6/04* (2006.01)
(52) U.S. Cl. .......................................... 378/37; 378/21
(58) Field of Classification Search ............. 378/21–27, 378/37
See application file for complete search history.

(56) References Cited

U.S. PATENT DOCUMENTS

| | | | |
|---|---|---|---|
| 2,842,706 A | 7/1958 | Dobischek et al. | |
| 3,617,285 A | 11/1971 | Staudenmayer | |
| 3,733,484 A | 5/1973 | Bayard | |
| 3,753,020 A | 8/1973 | Zingaro | |
| 3,783,288 A | 1/1974 | Barbour et al. | |
| 3,921,022 A | 11/1975 | Levine | |
| 4,012,656 A | 3/1977 | Norman et al. | |
| 4,253,221 A | 3/1981 | Cochran, Jr. et al. | |
| 4,289,969 A | 9/1981 | Cooperstein et al. | |
| 4,958,365 A | 9/1990 | Sohval et al. | |

(Continued)

FOREIGN PATENT DOCUMENTS

DE 197 00 992 7/1998

(Continued)

OTHER PUBLICATIONS

First Office Action from Japanese Patent Office dated Oct. 17, 2008 for Japanese Patent Application No. 2002-535152, based on PCT/US01/30027.

(Continued)

*Primary Examiner*—Courtney Thomas
(74) *Attorney, Agent, or Firm*—Jenkins,Wilson, Taylor & Hunt, P.A.

(57) ABSTRACT

Stationary x-ray digital breast tomosynthesis systems and related methods are disclosed. According to one aspect, the subject matter described herein can include an x-ray tomosynthesis system having a plurality of stationary field emission x-ray sources configured to irradiate a location for positioning an object to be imaged with x-ray beams to generate projection images of the object. An x-ray detector can be configured to detect the projection images of the object. A projection image reconstruction function can be configured to reconstruct tomography images of the object based on the projection images of the object.

46 Claims, 11 Drawing Sheets

U.S. PATENT DOCUMENTS

| | | |
|---|---|---|
| 5,129,850 A | 7/1992 | Kane et al. |
| 5,138,237 A | 8/1992 | Kane et al. |
| 5,305,363 A | 4/1994 | Burke et al. |
| 5,371,778 A | 12/1994 | Yanof et al. |
| 5,377,249 A | 12/1994 | Wiesent et al. |
| 5,424,054 A | 6/1995 | Bethune et al. |
| 5,557,105 A | 9/1996 | Honjo et al. |
| 5,578,821 A | 11/1996 | Meisberger et al. |
| 5,616,368 A | 4/1997 | Jin et al. |
| 5,623,180 A | 4/1997 | Jin et al. |
| 5,637,950 A | 6/1997 | Jin et al. |
| 5,648,699 A | 7/1997 | Jin et al. |
| 5,726,524 A | 3/1998 | Debe |
| 5,773,834 A | 6/1998 | Yamamoto et al. |
| 5,773,921 A | 6/1998 | Keesmann et al. |
| 5,834,783 A | 11/1998 | Muraki et al. |
| 5,844,963 A | 12/1998 | Koller et al. |
| 5,910,974 A | 6/1999 | Kuhn et al. |
| 5,973,444 A | 10/1999 | Xu et al. |
| 5,976,444 A | 11/1999 | Pearson et al. |
| 6,019,656 A | 2/2000 | Park et al. |
| 6,057,637 A | 5/2000 | Zettl et al. |
| 6,087,765 A | 7/2000 | Coll et al. |
| 6,250,984 B1 | 6/2001 | Jin et al. |
| 6,259,765 B1 | 7/2001 | Baptist |
| 6,271,923 B1 | 8/2001 | Hill |
| 6,277,138 B1 | 8/2001 | Levinson et al. |
| 6,280,697 B1 | 8/2001 | Zhou et al. |
| 6,297,592 B1 | 10/2001 | Goren et al. |
| 6,333,968 B1 | 12/2001 | Whitlock et al. |
| 6,334,939 B1 | 1/2002 | Zhou et al. |
| 6,385,292 B1 | 5/2002 | Dunham et al. |
| 6,440,761 B1 | 8/2002 | Choi |
| 6,445,122 B1 | 9/2002 | Chuang et al. |
| 6,456,691 B2 | 9/2002 | Takahashi et al. |
| 6,459,767 B1 | 10/2002 | Boyer et al. |
| 6,470,068 B2 | 10/2002 | Cheng |
| 6,498,349 B1 | 12/2002 | Thomas et al. |
| 6,553,096 B1 | 4/2003 | Zhou et al. |
| RE38,223 E | 8/2003 | Keesmann et al. |
| 6,630,772 B1 | 10/2003 | Bower et al. |
| 6,650,730 B2 | 11/2003 | Bogatu et al. |
| 6,674,837 B1 | 1/2004 | Taskar et al. |
| 6,760,407 B2 | 7/2004 | Price et al. |
| RE38,561 E | 8/2004 | Keesmann et al. |
| 6,850,595 B2 | 2/2005 | Zhou et al. |
| 6,852,973 B2 | 2/2005 | Suzuki et al. |
| 6,876,724 B2 | 4/2005 | Zhou et al. |
| 6,965,199 B2 | 11/2005 | Stoner et al. |
| 6,980,627 B2 | 12/2005 | Qiu et al. |
| 7,085,351 B2 | 8/2006 | Lu et al. |
| 7,227,924 B2 | 6/2007 | Zhou et al. |
| 7,359,484 B2 | 4/2008 | Qiu et al. |
| 2001/0019601 A1 | 9/2001 | Tkahashi et al. |
| 2002/0006489 A1 | 1/2002 | Goth et al. |
| 2002/0085674 A1 | 7/2002 | Price et al. |
| 2002/0110996 A1 | 8/2002 | Yaniv et al. |
| 2002/0140336 A1 | 10/2002 | Stoner et al. |
| 2002/0171357 A1 | 11/2002 | Sun et al. |
| 2003/0002627 A1 | 1/2003 | Espinosa et al. |
| 2003/0102222 A1 | 6/2003 | Zhou et al. |
| 2003/0198318 A1 | 10/2003 | Price et al. |
| 2004/0028183 A1 | 2/2004 | Lu et al. |
| 2004/0036402 A1 | 2/2004 | Keesmann et al. |
| 2004/0108298 A1 | 6/2004 | Gao |
| 2004/0114721 A1 | 6/2004 | Qiu et al. |
| 2004/0240616 A1 | 12/2004 | Qiu et al. |
| 2004/0256975 A1 | 12/2004 | Gao et al. |
| 2005/0028554 A1 | 2/2005 | Wanner et al. |
| 2005/0133372 A1 | 6/2005 | Zhou et al. |
| 2005/0175151 A1 | 8/2005 | Dunham et al. |
| 2005/0226371 A1* | 10/2005 | Kautzer et al. ............. 378/37 |
| 2005/0269559 A1 | 12/2005 | Zhou et al. |
| 2005/0281379 A1 | 12/2005 | Qiu et al. |
| 2007/0009081 A1 | 1/2007 | Zhou et al. |

FOREIGN PATENT DOCUMENTS

| | | |
|---|---|---|
| DE | 101 64 315 A1 | 8/2002 |
| DE | 101 64 318 A1 | 8/2002 |
| JP | 53103392 A | 9/1978 |
| JP | 57162431 A2 | 10/1982 |
| JP | 60254615 A2 | 12/1985 |
| JP | 06163381 A2 | 6/1994 |
| JP | 08264139 A | 10/1996 |
| JP | 09180894 A | 7/1997 |
| JP | 2000251826 A2 | 2/1999 |
| JP | 11-111158 | 4/1999 |
| JP | 11-260244 | 9/1999 |
| JP | 2002-208028 | 7/2000 |
| JP | 2001190550 A | 7/2001 |
| JP | 2001250496 A | 9/2001 |
| TW | 00319886 | 11/1997 |
| TW | 0379354 B | 1/2000 |
| TW | 0439303 B | 6/2001 |
| TW | 0527624 B | 4/2003 |
| TW | 0529050 B | 4/2003 |
| WO | WO 00/51936 A3 | 9/2000 |
| WO | WO02/03413 | 1/2002 |
| WO | WO 02/31857 | 4/2002 |
| WO | WO 03/012816 A2 | 2/2003 |

OTHER PUBLICATIONS

Confirmation of issuance of Chinese Patent No. ZL001820211.X corresponding to PCT/US01/30027.

Notice of Publication for Chinese Patent Application No. 200810215733.1. Publication No. 101352353, Publication date Jan. 28, 2009.

Abstract of JPA H11-116218.

Abstract of JPA H09-180894.

Abstract of JPA 2001-048509.

Abstract of JPA S61-142644.

Abstract of JPA S54-027793.

Confirmation that Chinese Application 093102622 issued on Mar. 1, 2009 as Patent No. I307110.

Final Rejected has been issued from the Japanese Patent Office dated Mar. 30, 2009 for Japanese Patent Application No. 2003-562962 based on PCT/US03/00537.

First Office Action from Chinese Patent Office dated Apr. 24, 2009 for Chinese Patent Application No. 200710003710.X.

Office Action from Canadian Patent Office dated May 27, 2008 for Canadian Application No. 2,424,826.

Notification of non-acceptance of amended claims dated Apr. 25, 2008 from Chinese Patent Office for Chinese Patent Application No. 03806739.0 (PCT/US03/00537).

Office Action from Japanese Patent Office for Japanese Patent Application No. 2003-562962 for corresponding PCT No. US03/00537.

W. Zhu et al., "Large Current Density from Carbon Nanotube Filed Emitters", *Appl. Phys. Lett.*, American Institute of Physics, vol. 75, No. 6, Aug. 9, 1999, pp. 873-875.

Radiologic Science for Technologist, Physics, Biology, and Protection, 6th Edition, S.C. Bushong, Mosby, Inc., 1997 (excerpt relating to focusing and thermionic emission).

Zhu et al., "Low-Field Electron Emission from Updoped Nanostructured Diamond", *Science*, vol. 282, 1471-1 473 (Nov. 20, 1998).

Brodie et al., "Vacuum Microelectronics", *Advance in Electronics and Electron Physics*, edited by P.W. Hawkes, vol. 83, pp. 1-106 (1992).

Okano et al., "Electron emission from nitrogen-doped pyramidal-shape diamond and its battery operation", *Appl. Phys. Lett.*, vol. 70, No. 16, pp. 2201-2203 (Apr. 21, 1997).

Okano et al., "Fabrication of a diamond field emitter array", *Appl. Phys. Lett.*, vol. 64, No. 20, pp. 2742-2744 (May 16, 1994).

Kumar et al., "Diamond-based field emission flat panel displays", *Solid State Technology*, Vo. 38, pp. 71-74 (May 1995).

Geis et al., "Diamond emitters fabrication and theory", *J. Vac. Sci. Technol. B*, vol. 14, No. 3, pp. 2060-2067, May/Jun. 1996.

Rinzler et al., "Unraveling Nanotubes: Field Emission from an Atomic Wire", *Science*, vol. 269, pp. 1550-1553 (Sep. 15, 1995).

de Heer et al., "A Carbon Nanotube Field-Emission Electron Source", *Science*, vol. 270, pp. 1179-1180 (Nov. 17, 1995).

Okazaki et al., "A New Emission Spectrum of $Au_2$ in the Gas Evaporation Technique: 761-809 nm", *Jpn. J. Appl. Phys.*, vol. 37, Pt. 1, No. 1, pp. 349-350 (Jan. 1998).

Wang et al., "Field emission from nanotube bundle emitters at low fields", *Appl. Phys. Lett.*, vol. 70, No. 24, pp. 3308-3310 (Jun. 16, 1997).

Yagishita et al., "Effects of Cleavage on Local Cross-Sectional Stress Distribution in Trench Isolation Structure", *Jpn. J. Appl. Phys.*, vol. 36, pp. 1335-1340 (Mar. 1997).

Wang et al., "A nanotube-based field-emission flat panel display", *Appl. Phys. Lett.*, vol. 72, No. 2, pp. 2912-2913 (Jun. 1, 1998).

Bonard et al., "Field emission from single-wall carbon nanotube films", *Appl. Phys. Left.*, vol. 73, No. 7, pp. 918-920 (Aug. 17, 1998).

A. Thess et al., "Crystalline Ropes of Metallic Carbon Nanotubes", *Science*, vol. 273, pp. 483-487 (Jul. 26, 1996).

C. Bower et al., "Synthesis and structure of pristine and alkali-metal-intercalated single-walled carbon nanotubes", *Appl. Phys.*, A 67, pp. 47-52 (1998).

X. P. Tang et al., "Electronic Structures of Single-Walled Carbon Nanotubes Determined by NMR", *Science*, vol. 288, pp. 492-494 (Apr. 21, 2000).

C. Journet et al., "Large-scale production of single-walled carbon nanotubes by the electric-arc technique", *Nature*, vol. 388, pp. 756-760 (Aug. 21, 1997).

A.M. Cassell et al., "Large Scale CVD Synthesis of Single-Walled Carbon Nanotubes", *J. Phys. Chem.*, B 103, pp. 6484-6492 (Jul. 20, 1999).

International Search Report for Application No. PCT/US05/03991 dated Jun. 22, 2006.

International Search Report for Application No. PCT/US03/00537 dated Apr. 10, 2003.

Taiwanese Office Action for Taiwan Patent No. 093102622 dated Dec. 21, 2007.

Chinese Office Action for Patent Application No. 03806739.0 dated Oct. 19, 2007.

Chinese Office Action dated Mar. 14, 2008 for Chinese Patent Application No. 01820211.X(PCT/US01/30027).

Examination Report from European Patent Office dated Mar. 3, 2008 for European Patent Application No. 03702044.3.

Korean Intellectual Property Office (KIPO) Office Action for Korean Patent Application No. 10-2004-7011373 dated Jun. 11, 2007.

Korean Intellectual Property Office (KIPO) Office Action for Korean Patent Application No. 10-2003-700004987 dated Jul. 19, 2007.

European Patent Office Examination Report dated Jun. 28, 2007 for European Patent Application No. 03702044.3.

Korean Office Action for Korean Patent Application No. 10-2004-7011373 dated Dec. 18, 2007.

International Search Report and Written Opinion for PCT Application No. PCT/US08/70477 dated Oct. 1, 2008.

Office Action from Japanese Patent Office for Japanese Patent Application No. 2003-580561 for corresponding PCT No. US03/06345 dated Sep. 3, 2008.

Non-final Office Action for U.S. Appl. No. 09/679,303 dated Jan. 16, 2002.

Final Office Action for U.S. Appl. No. 09/679,303 dated May 6, 2002.

Non-final Office Action for U.S. Appl. No. 09/679,303 dated Aug. 20, 2002.

Notice of Allowance for U.S. Appl. No. 09/679,303 dated Nov. 1, 2002.

Office Communication for U.S. Appl. No. 09/679,303 dated Feb. 6, 2003.

Non-final Office Action for U.S. Appl. No. 10/051,183 dated Sep. 10, 2003.

Non-final Office Action for U.S. Appl. No. 10/051,183 dated Apr. 21, 2004.

Notice of Allowance for U.S. Appl. No. 10/051,183 dated Aug. 31, 2004.

Office Communication for U.S. Appl. No. 10/051,183 dated Jan. 14, 2005.

Non-final Office Action for U.S. Appl. No. 10/970,384 dated Apr. 8, 2008.

Office Action-Restriction requirement for U.S. Appl. No. 11/051,332 dated Sep. 7, 2006.

Notice of Allowance dated for U.S. Appl. No. 11/051,332 dated Dec. 28, 2006.

Non-final Office Action for U.S. Appl. No. 10/309,126 dated May 22, 2003.

Non-final Office Action for U.S. Appl. No. 10/309,126 dated Nov. 5, 2003.

Non-final Office Action for U.S. Appl. No. 10/309,126 dated Apr. 20, 2004.

Notice of Allowance for U.S. Appl. No. 10/309,126 dated Aug. 26, 2004.

Corrected Notice of Allowance for U.S. Appl. No. 10/309,126 dated Sep. 14, 2004.

Non-final Office Action for U.S. Appl. No. 10/358,160 dated Sep. 21, 2004.

Non-final Office Action U.S. Appl. No. 10/358,160 dated Jun. 7, 2005.

Office Action—Restriction requirement U.S. Appl. No. 10/358,160 dated Oct. 26, 2005.

Notice of Allowance U.S. Appl. No. 10/358,160 dated Feb. 8, 2006.

Non-final Office Action for U.S. Appl. No. 11/415,953 dated Dec. 11, 2007.

Office Action-Restriction requirement for U.S. Appl. No. 11/415,953 dated May 22, 2008.

Decision on Granting of Patent Right has been issued from the Chinese Patent Office for Chinese Patent Application No. 01820211.X (PCT/US01/30027 dated Sep. 26, 2008.

Second Office Action from Japanese Patent Office dated Dec. 7, 2009 for Japanese Patent Application No. 2002-535152.

Decision on Rejection issued from the Chinese Patent Office dated Dec. 11, 2009 for Chinese Application No. 200710003710.X.

Office Action-Final for U.S. Appl. No. 11/441,281 dated Jun. 4, 2009.

Supplementary European Search Report for European Patent Application No. 01981327.8 dated Jun. 22, 2009.

* cited by examiner

STATIONARY X-RAY DIGITAL BREAST TOMOSYNTHESIS SYSTEMS AND RELATED METHODS

RELATED APPLICATION

The presently disclosed subject matter claims the benefit of U.S. Provisional Patent Application Ser. No. 60/961,175, filed Jul. 19, 2007, the disclosure of which is incorporated herein by reference in its entirety.

GOVERNMENT INTEREST

This presently disclosed subject matter was made with U.S. Government support under Grant No. US4CA119343 awarded by the National Cancer Institute. Thus, the U.S. Government has certain rights in the presently disclosed subject matter.

TECHNICAL FIELD

The subject matter described herein relates to x-ray radiography. More specifically, the subject matter describes stationary x-ray digital breast tomosynthesis systems and related methods.

BACKGROUND

Mammography is currently the most effective screening and diagnostic tool for early detection of breast cancer, and has been attributed to the recent reduction of breast cancer mortality rate. However, the nature of the two-dimensional mammogram makes it difficult to distinguish a cancer from overlying breast tissues, and the interpretation can be variable among radiologists. A higher rate of false positive and false-negative test results exist because the dense tissues interfere with the identification of abnormalities associated with tumors. Digital breast tomosynthesis (DBT) is a three-dimensional imaging technique that is designed to overcome this problem. It is a limited angle tomography technique that provides reconstruction planes in the breast using projection images from a limited angular range.

Several prototype DBT scanners have been manufactured by commercial vendors. The system designs are based on a full-field digital mammography (FFDM) unit. A mammography x-ray tube is used to collect the projection images by moving 10-50 degrees around the object. The reported total scanning time is 7-40 seconds depending on the number of views and the thickness of the breast, which is much longer than that of the regular mammography. The long imaging time can cause patient motion blur which degrades image quality and can make patients uncomfortable. Further, the power of the x-ray source, gantry rotating speed and detector frame rate limit the scanning speed of the current DBT systems.

DBT systems utilize the standard mammography x-ray tube with about a 300 µm x-ray focal spot size. Due to the gantry rotation and mechanical instability, the effective focal spot size during image acquisition is larger than the static value which degrades the image resolution. Two gantry rotation modes have been developed. One commercially-available system uses a stop-and-shoot technique. The gantry makes a full stop before taking each projection image. Acceleration/deceleration can cause mechanical instability of the system. A continuous rotation mode is used in other commercially available systems. The gantry keeps a constant rotation speed during the whole imaging process. In this case, the x-ray focal spot size is enlarged along the motion direction. The value of the enlargement depends on the rotation speed and the exposure time. It has been reported that the x-ray focal spot moves about 1 mm in a typical scan. This does not leave room for further reduction of the total scanning time, which will require a faster gantry rotation and a larger focal spot blurring.

It would be beneficial to provide x-ray imaging systems and methods having reduced data collection times and improvements for patient comfort. One or more such improvements can enable new applications for x-ray imaging of breast tissue as well as other objects. Accordingly, it is desirable to provide x-ray imaging systems and methods having one or more of these improvements.

In addition, current clinical mammography scanners use polychromatic x-ray radiation with slight energy filtering. It is known that monochromatic and quasi-monochromatic radiation provides better imaging quality and can potentially reduce the imaging dose. Currently, there is no effective way, however, to generate monochromatic or quasi-monochromatic radiation in a clinical environment that can provide sufficient x-ray photo flux. Accordingly, it is desirable to provide x-ray imaging systems and methods that can perform monochromatic or quasi-monochromatic imaging in a clinically acceptable scanning speed.

SUMMARY

It is an object of the presently disclosed subject matter to provide novel stationary x-ray digital breast tomosynthesis systems and related methods.

An object of the presently disclosed subject matter having been stated hereinabove, and which is achieved in whole or in part by the presently disclosed subject matter, other objects will become evident as the description proceeds when taken in connection with the accompanying drawings described hereinbelow.

BRIEF DESCRIPTION OF THE DRAWINGS

The subject matter described herein will now be explained with reference to the accompanying drawings, of which.

DETAILED DESCRIPTION

Figure 1:
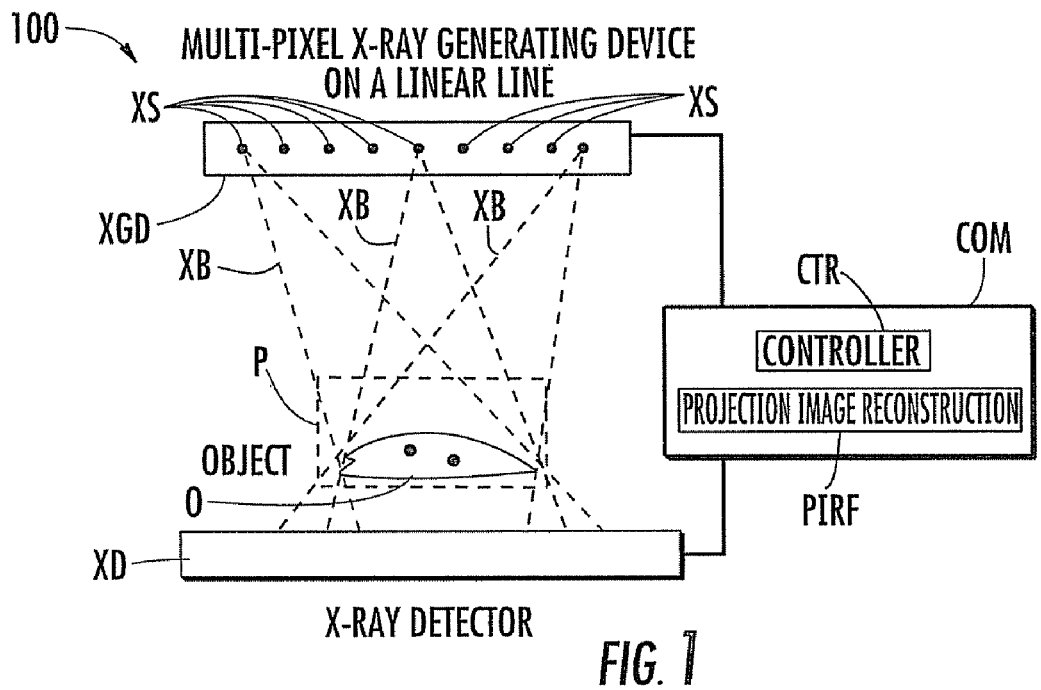
FIG. 1 is a schematic diagram of a MBFEX system according to an embodiment of the subject matter described herein.

The subject matter disclosed herein is directed to multi-beam field emission x-ray (MBFEX, also referred to as multi-pixel field emission x-ray) systems and techniques that can utilize a plurality of field emission x-ray sources, an x-ray detector, and projection image reconstruction techniques. Particularly, the systems and techniques disclosed herein according to one aspect can be applied to x-ray digital tomosynthesis. In accordance with one embodiment, a plurality of field emission x-ray sources can irradiate a location for positioning an object to be imaged with x-ray beams for generating projection images of the object. An x-ray detector can detect the projection images of the object. A projection image reconstruction function can reconstruct tomography images of the object based on the projection images of the object. The subject matter disclosed herein enables increased scanning speed, a simplification of system design, and image quality enhancements.

In one application, the subject matter disclosed herein can be a stationary digital breast tomosynthesis (DBT) system that utilizes a carbon nanotube based MBFEX system. The MBFEX system can include an array of individually programmable x-ray pixels that can be substantially evenly placed to cover a wide field of view. Projection images can be acquired by electronically switching on and off the individual x-ray pixels without mechanical motion of any of the x-ray source, the detector, or the object.

In one embodiment of the subject matter described herein, projection images of an object can be collected sequentially, one at a time, from different viewing angles by electronically switching on and off individual x-ray source pixels. The x-ray source pixels can be spatially distributed. Each pixel can be switched on for a predetermined time and a predetermined current to deliver a predetermined amount of dosage to the object. The transmitted x-ray intensity from a particular x-ray source pixel can be detected and recorded by an x-ray detector. The spacing between the x-ray beam pixels and the number of pixels can be varied to provide angular coverage and the number of projection images desired. The projection images collected from different viewing angles can be processed to reconstruct tomography images of the object to reveal the internal structure of the object. In one example, the x-ray source can include a total of between about ten and one-hundred x-ray focal spots (e.g., twenty-five (25) x-ray source pixels) positioned along an arc that can cover a viewing range of between about 10 and 100 degrees (e.g., 30-50 degree viewing range). The focal spots define a plane that is substantially perpendicular to an imaging plane of the x-ray detector.

In one embodiment of the subject matter described herein, one or a plurality of monochromators can be used to generate monochromatic x-ray radiation for imaging an object. Such monochromatic x-ray radiation can be produced using Bragg diffraction. Quasi-monochromatic x-ray beams can be generated by placing filters in front of an x-ray window that receives polychromatic x-ray radiation. By selecting the filtering material and thickness of the material, quasi-monochromatic radiation with a narrow energy window can be produced. This, however, typically includes the use of $200^{th}$ to $500^{th}$ value layer filtering material. This means that 99.5 to 99.8% of the x-ray intensity is attenuated by the filter. The low x-ray flux has prevented the use of monochromatic x-ray radiation for clinical imaging.

In one example of monochromatic x-ray radiation, the generated monochromatic x-ray radiation can be utilized for imaging a breast. An advantage of monochromatic and quasi-monochromatic x-ray radiation includes improved imaging quality at reduced x-ray dose, which is important for breast imaging. The subject matter described herein can enable physicians to image human breasts using quasi-monochromatic x-ray radiation at an imaging speed that is comparable to commercially-available DBT scanners with polychromatic x-ray radiation.

One technique to overcome the obstacles of low flux and therefore long imaging time is to combine multi-beam field emission x-ray source with multiplexing x-ray imaging. Cone beam quasi-monochromatic radiation can be produced by heavy filtering. The pixilated and spatially distributed MBFEX source can generate x-ray beams from multiple projection angles without mechanical motion. A stationary DBT scanner operating in the sequential scanning mode can provide a full scan of 25 views using 85 mAs total dose with a speed that is a factor of 10 faster than the C-arm based DBT scanners at a comparable dose. Experiments have also shown that the parallel multiplexing imaging process provides a factor of N/2 (N=number of x-ray pixels) increase of the imaging speed comparing to the conventional serial imaging technique used for tomography. The combination of the gains from stationary design and multiplexing described herein (about ×100) can compensate for the loss of x-ray flux due to the use of heavy filtering ($100^{th}$ value layer) which enables the qM-DBT scanner to operate at a comparable scanning time as commercially-available C-arm based system, but with a better imaging quality and a reduced imaging dose.

As referred to herein, the term "nano-structured" or "nano-structure" material can designate materials including nano-particles with particle sizes less than 100 nm, such as nano-tubes (e.g., carbon nanotubes). These types of materials have been shown to exhibit certain properties that have raised interest in a variety of applications.

As referred to herein, the term "multi-beam x-ray source" can designate devices that can simultaneously or sequentially generate multiple x-ray beams, For example, the "multi-beam x-ray source" can include a field emission based multi-beam x-ray source having electron field emitters. The electron field emitters can include nano-structured materials based materials.

FIG. 1 is a schematic diagram of a MBFEX system generally designated 100 according to an embodiment of the subject matter described herein. Referring to FIG. 1, system 100 can include a computer COM having a controller CTR configured to control an x-ray generating device XGD and an x-ray detector XD for imaging an object O to be imaged. X-ray generating device XGD can include a plurality of individually-controllable, field emission x-ray sources XS configured to irradiate object O with x-ray beams XB for generating projection images of object O.

X-ray sources XS can be positioned for directing x-ray beams XB towards a location or position P (designated by broken lines) at which object O can be placed. The x-ray beams can be directed towards position P from several different angles. Further, x-ray sources XS, x-ray detector XD, and position P are positioned such that the generated projection images are detected by x-ray detector XD. X-ray sources XS are positioned along a substantially straight line formed by x-ray generating device XGD such that the generated x-ray beams are directed substantially towards position P and can pass through the area within position P. The line can be parallel to an imaging plane of the x-ray detector. As described in further detail below, x-ray sources XS can be arranged in any suitable position such that the x-ray beams are directed substantially towards position P and the projection images are detected by x-ray detector XD. The x-ray sources and x-ray detector can be stationary with respect to one another during irradiation of an object by the x-ray sources and detection of the projection images by the x-ray detector. The x-ray sources can be controlled for sequential activation one at a time for a predetermined dwell time and predetermined x-ray dose.

After passing through object O at position P, x-ray beams XB can be detected by x-ray detector XD. X-ray detector XD can be a high frame rate, digital area x-ray detector configured to continuously capture x-ray beams XB. After all or at least a portion of x-ray beams XB are collected and stored as x-ray signal data in a memory, a projection image reconstruction function PIRF can reconstruct tomography images of object O based on the projection images of the object O.

The tomography images can be constructed by using a suitable technique to obtain multi-projection images of an object from multiple x-ray sources using a single detector. Common techniques include shift-and-add, filtered back projection, ordered subsets convex maximum likelihood, etc.

Figure 2:
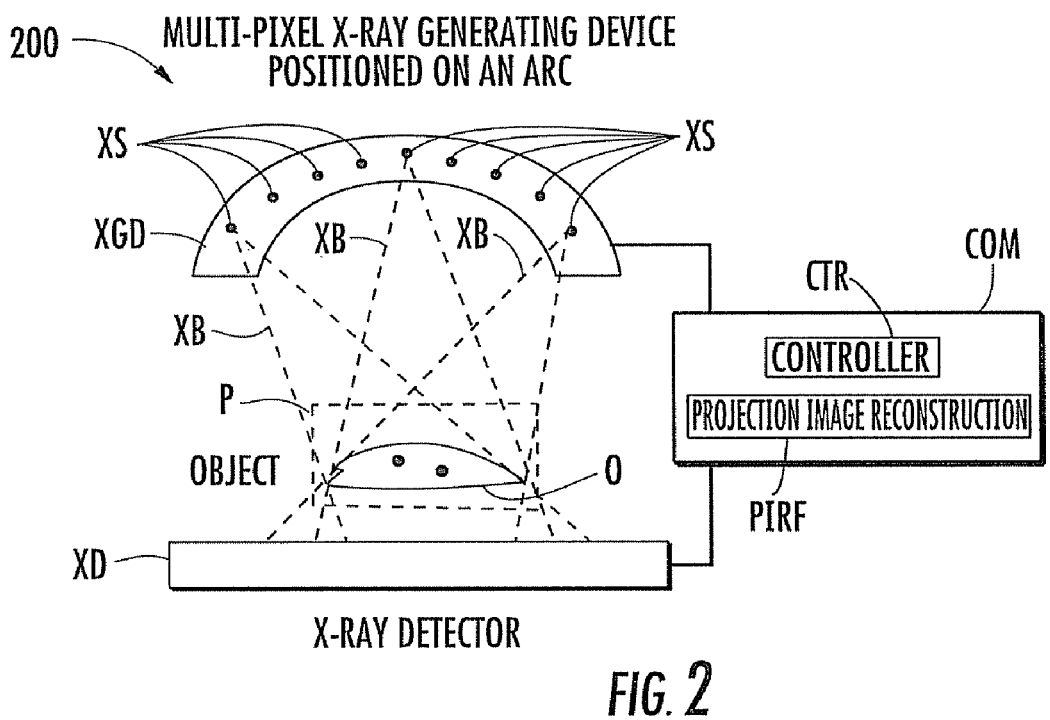
FIG. 2 is a schematic diagram of a MBFEX system having x-ray sources positioned along a linear line according to an embodiment of the subject matter described herein.

According to another aspect of the subject matter disclosed herein, x-ray sources can be positioned along an arc defined by the x-ray generating device. The arc can define a plane that can be substantially perpendicular to an imaging plane of the x-ray detector. FIG. 2 is a schematic diagram of a MBFEX system generally designated 200 having x-ray sources XS positioned along a linear line according to an embodiment of the subject matter described herein. Referring to FIG. 2, x-ray sources XS can be positioned at least substantially along a linear line formed by x-ray generating device XGD. X-ray sources XS can be positioned for directing x-ray beams XB towards and through position P at which object O can be placed. The x-ray beams can be directed to position P from several different angles. Further, x-ray sources XS, x-ray detector XD, and position P can be positioned such that the generated projection images are detected by x-ray detector XD. After passing through object O at position P, x-ray beams XB can be detected by x-ray detector XD. After all or at least a portion of x-ray beams XB are collected and stored as x-ray signal data in a memory, a projection image reconstruction function PIRF can reconstruct tomography images of object O based on the projection images of the object O.

Figure 3:
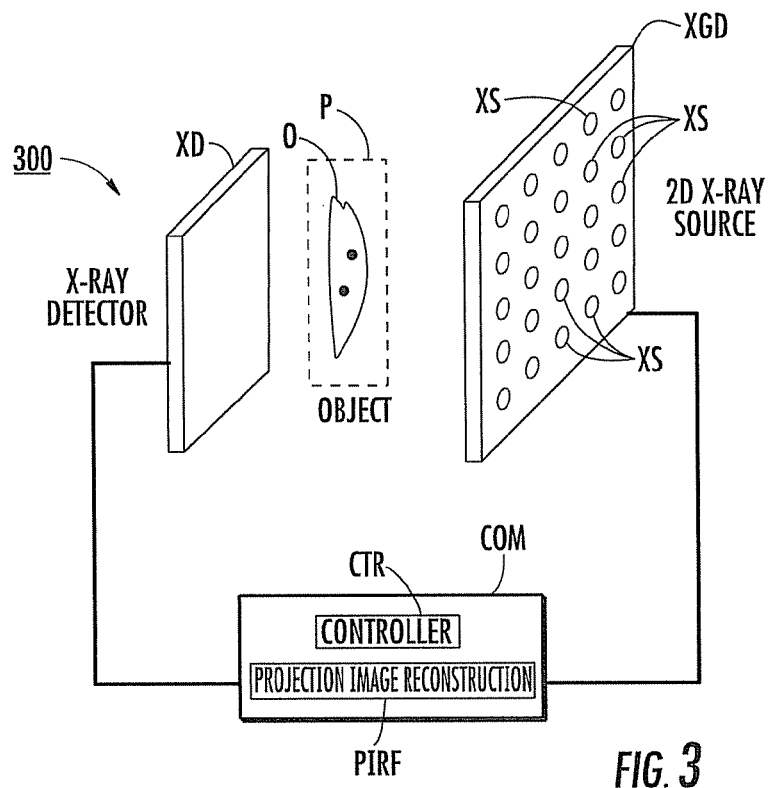
FIG. 3 is a schematic diagram of a MBFEX system having x-ray sources positioned along a two-dimensional plane according to an embodiment of the subject matter described herein.

According to another aspect of the subject matter disclosed herein, x-ray sources can include focal spots positioned along a two-dimensional plane or matrix on an x-ray anode. FIG. 3 is a schematic diagram of a MBFEX system generally designated 300 having x-ray sources XS positioned along a two-dimensional plane according to an embodiment of the subject matter described herein. Referring to FIG. 3, x-ray sources XS can be positioned substantially along a two-dimensional plane formed by x-ray generating device XGD. X-ray sources XS can be positioned for directing x-ray beams XB towards and through position P at which object O can be placed. The x-ray beams can be directed to position P from several different angles. Further, x-ray sources XS, x-ray detector XD, and position P are positioned such that the generated projection images are detected by x-ray detector XD. After passing through object O at position P, x-ray beams XB can be detected by x-ray detector XD. After all or at least a portion of x-ray beams XB are collected and stored as x-ray signal data in a memory, a projection image reconstruction function PIRF can reconstruct tomography images of object O based on the projection images of the object O.

Figure 4A:
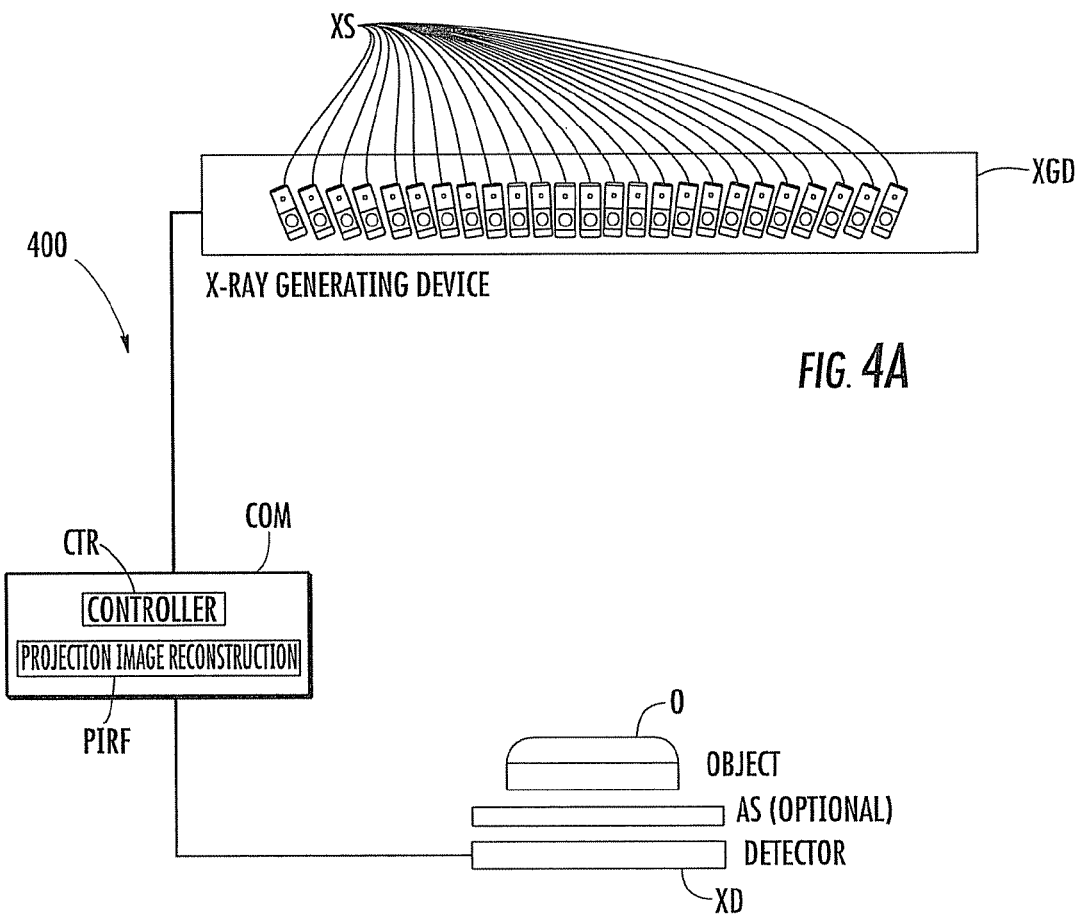
FIG. 4A is a schematic diagram of a MBFEX system having x-ray sources positioned along a line, evenly spaced, and angled for directing x-ray beams towards an object according to an embodiment of the subject matter described herein.

According to another aspect of the subject matter disclosed herein, x-ray sources can be positioned along a line, evenly spaced, and angled for directing x-ray beams towards an object. FIG. 4A is a schematic diagram of a MBFEX system generally designated 400 having x-ray sources XS positioned along a line, evenly spaced, and angled for directing x-ray beams towards an object according to an embodiment of the subject matter described herein. Referring to FIG. 4A, x-ray sources XS can be gated carbon nanotube emitting pixels positioned substantially along a two-dimensional plane formed by x-ray generating device XGD. In this example, the x-ray generating device includes twenty-five (25) x-ray sources in total, although the x-ray generating device can alternatively include any suitable number of x-ray sources, more or less even that twenty-five in number.

The x-ray source can be housed in a vacuum chamber having a 30 μm thick molybdenum (Mo) window. The window can function as a radiation filter. Each pixel can comprise a carbon nanotube cathode, a gate electrode to extract the electrons, and a set of electron focusing lenses (e.g., Einzel-type electrostatic focusing lenses) to focus the field emitted electrons to a small area (focal spot) on the target. The focal spots can be substantially the same size. The sizes of the focal spots and/or the x-ray flux generated by the x-ray sources can be adjusted by the controller. Alternatively, the focal spots can range between about 0.05 mm and 2 mm in size. The system is designed for an isotropic 0.2×0.2 mm effective focal spot size for each x-ray source pixel. The individual focal spot size can be adjusted by adjusting the electrical potentials of the focusing electrodes. To minimize the current fluctuation and delay and to reduce pixel to pixel variation, an electrical compensation loop can be incorporated to automatically adjust the gate voltage to maintain a constant pre-set emission current. The area of the carbon nanotube cathode can be selected such that a peak x-ray tube current of about 10 mA can be obtained with the effective focal spot size of 0.2×0.2 mm. A higher x-ray peak current of 50-100 mA can be obtained by increasing the carbon nanotube area and the focal spot size.

X-ray sources XS can be positioned for directing x-ray beams XB towards position P at which object O is placed. The x-ray beams can be directed towards and through position P from several different angles. Further, x-ray sources XS, x-ray detector XD, and position P are positioned such that the generated projection images are detected by x-ray detector XD. To collect the projection images of object O from different angles for tomosynthesis, controller CTR can sequentially activate an array of electron emitting pixels, as described in further detail below, which are spatially distributed over a relatively large area. X-ray sources XS are positioned such that the generated x-ray beams are directed at least substantially to position P. Each x-ray source XS can include a field emitter operable to generate an electron beam and operable to direct the electron beam to a focal point of a target. The emitted electron beam can be accelerated to the target where a scanning x-ray beam originates for different points over a large area of the target. The controller CTR can further vary the intensity of the x-ray radiation based on the distance between x-ray source XS and object O such that the x-ray dose delivered to object O from every viewing angle is the same.

X-ray sources XS can be positioned such that x-ray generating device XGD provides a substantially even 2 degree angular spacing between the x-ray focal spots at a source-to-detector distance of about 64.52 cm. The position and the orientation of the individual x-ray target can be such that the center axis of a generated x-ray cone beam goes through an iso-center OC, which can either be a location on object O to be imaged or a point on x-ray detector XD. The cone-shaped x-ray beams can have substantially the same x-ray intensity distribution on the object. Further, x-ray sources can produce x-ray radiation having different energy spectra.

After passing through object O at position P, x-ray beams XB can be detected by x-ray detector XD. After all or at least a portion of x-ray beams XB are collected and stored as x-ray signal data in a memory, a projection image reconstruction function PIRF can reconstruct tomography images of object O based on the projection images of the object O.

Figure 4B:
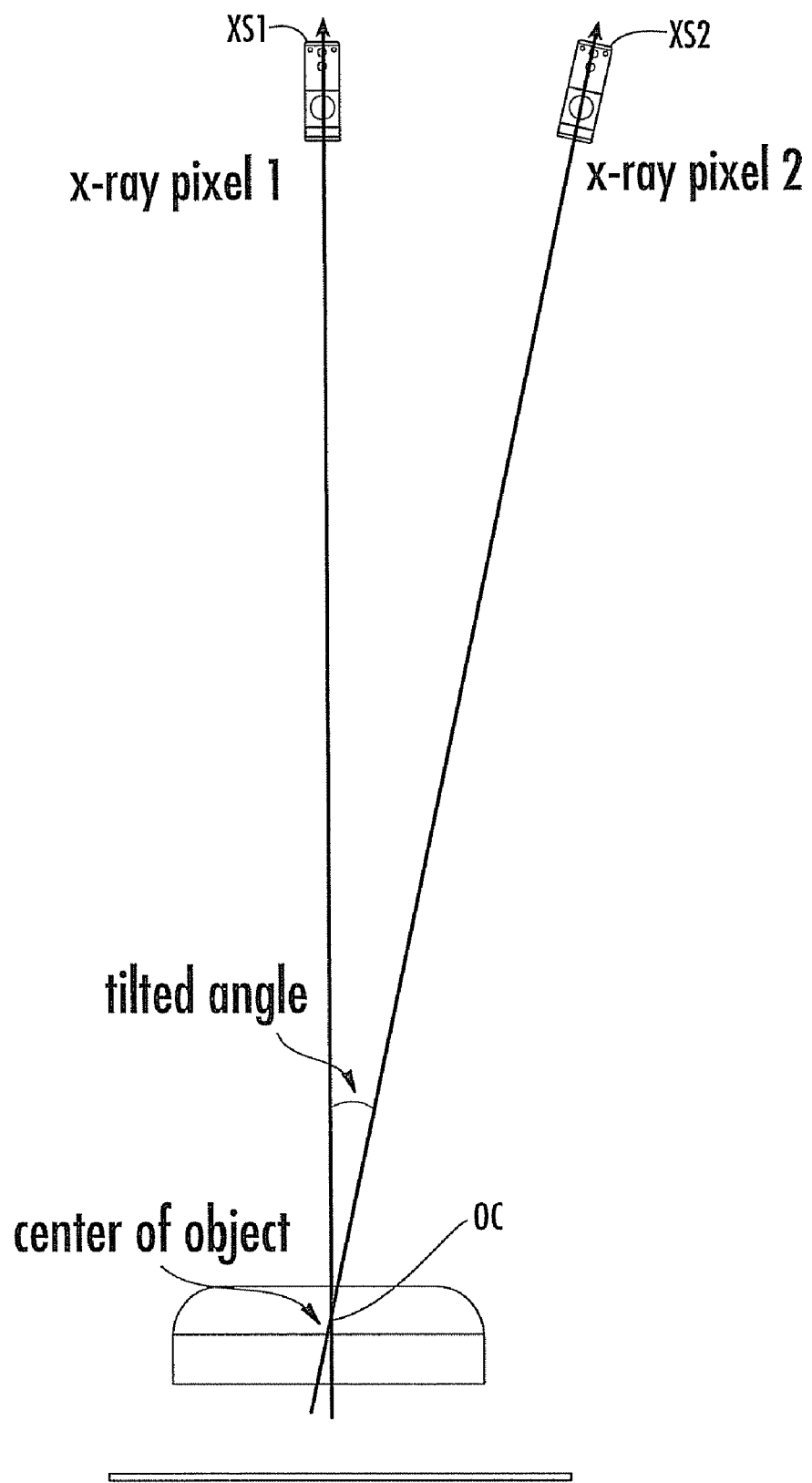
FIG. 4B is a schematic diagram of two x-ray source pixels of the system shown in FIG. 4A according to an embodiment of the subject matter described herein.

FIG. 4B is a schematic diagram of two x-ray source pixels of system 400 shown in FIG. 4A according to an embodiment of the subject matter described herein. Referring to FIG. 4B, x-ray sources XS1 and XS2 are angled towards an iso-center OC of object O. The line formed by center OC of object O and an x-ray focal spot of an electron field emitter of each x-ray source is on a symmetric plane of the x-ray source. The x-ray source pixels can be tilted such that the central line of the x-ray beams generated by the x-ray source pixels are directed towards iso-center OC. In one example, the central lines of x-ray sources XS1 and XS2 form a tilted angle. The x-ray sources can be tilted with respect to one another to achieve a desired tilted angle.

In system 400, the x-ray beam originating from a focal point can be generated by the electron beam from a corresponding pixel on a cathode. A scanning x-ray beam can be generated by sequentially activating individual pixels. A constant high DC voltage (about 0-100 KVp) can be applied between the x-ray anode and the gate electrode. A variable DC voltage (about 0-2 kV) can be applied on the gate electrode. Alternatively, the x-ray anodes can be configured at different voltages to produce x-ray radiation with multiple energies. For example, for a system having 25 x-ray sources, 12 anodes can be configured at low voltage, and 13 anodes can be configured at high voltage. Such a configuration enables the system for dual-energy imaging.

Switching on and off the individual emitting pixel can be effected by an electronic circuit (e.g., a MOSFET circuit) connected to the cathode. The electronic circuit can be used to individually control the x-ray intensities from the different x-ray focal spots XS (e.g., x-ray sources XS1 and XS2) such that they can either be the same or be modulated to deliver a desired intensity or intensity distribution on object O to be imaged. An x-ray beam can be produced from a corresponding focal point when the electron beam bombards the anode surface of the target. To generate a scanning beam, a pulsed voltage with a predetermined pulse width can be scanned across the individual MOSFETs. At each point, the channel can be "opened" to generate an electron beam from the pixel, which can lead to the generation of an x-ray beam from the corresponding focal point on the target. To minimize the fluctuation of the x-ray flux, the cathode can be operated at a constant current mode. The gate voltage can be adjusted automatically to maintain the emission current and thus x-ray flux from each pixel to within a desired level.

The 25 x-ray source pixels of x-ray generating device XGD can span a distance of 57.45 cm from end-to-end. At a source-to-object distance of 64.52 cm, the device provides 48 degree coverage with a substantially even 2 degree angular spacing between adjacent pixels. The linear spacing between adjacent x-ray source pixels can vary to provide even angular spacing. The x-ray beams can be collimated to a 23.04 cm field-of-view (FOV) at the phantom plane. If the x-ray source pixels are arranged in a linear line parallel to the detector plane rather than an arc, the pixel-to-source distance can vary from pixel to pixel. In one option to compensate this variation in x-ray beam traveling distance, the x-ray tube current from each pixel can be individually adjusted such that the flux at the phantom surface remains the same. In another solution, the image intensities can be normalized in the reconstruction process. The phantom can be placed on a stage for positioning with a 2.54 cm air gap between the detector and the phantom.

Figure 5:
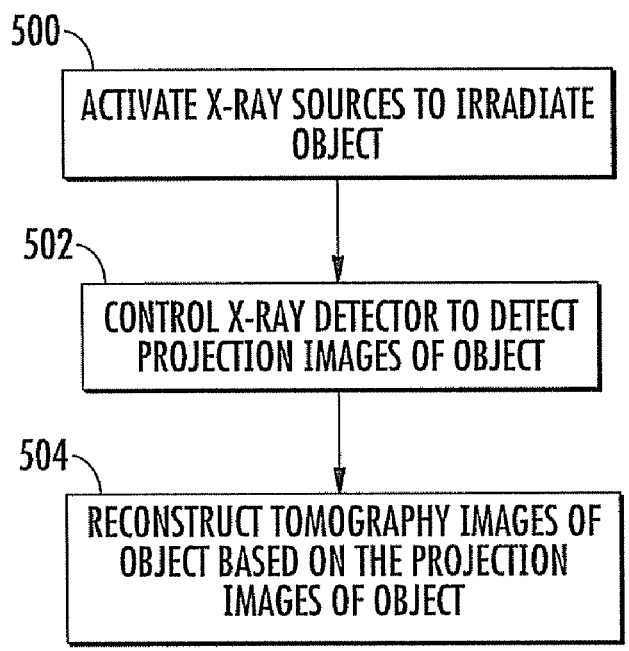
FIG. 5 is a flow chart of an exemplary process of acquiring object images according to an embodiment of the subject matter disclosed herein.

FIG. 5 is a flow chart illustrating an exemplary process of acquiring object images according to an embodiment of the subject matter disclosed herein. System 100 is referenced in this example, although any other system described herein may utilize the process for acquiring object images. Referring to FIGS. 1 and 5, controller CTR can activate x-ray sources XS to irradiate object O with x-ray beams for generating projection images of object O (block 500). At block 502, controller CTR can control x-ray detector XD to detect the projection images of object O. At block 504, projection image reconstruction function PIRF can reconstruct tomography images of object O based on the projection images of object O. Any suitable technique can be utilized by function PIRF for reconstructing the tomography images of object O.

Figure 6:
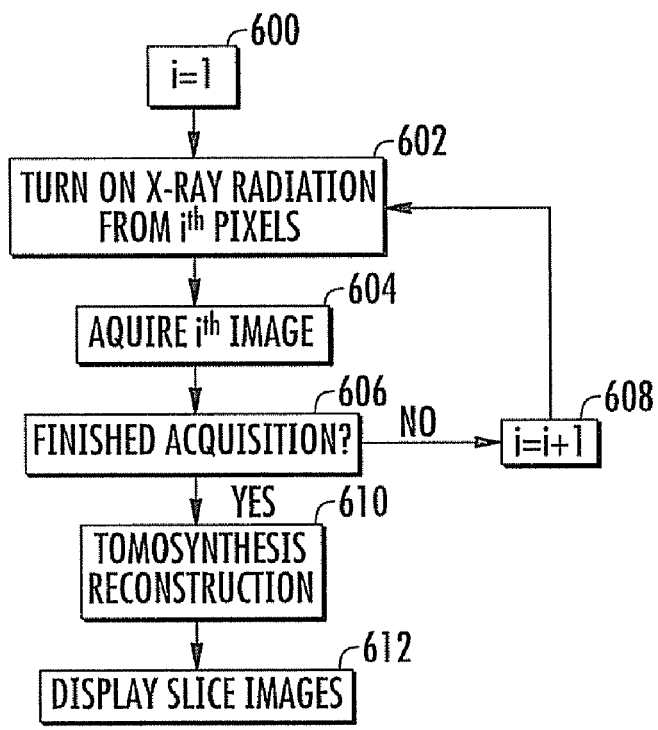
FIG. 6 is a flow chart of an exemplary process of sequentially acquiring object images utilizing a MBFEX system according to an embodiment of the subject matter disclosed herein.

FIG. 6 is a flow chart illustrating an exemplary process of sequentially acquiring object images utilizing a MBFEX system according to an embodiment of the subject matter disclosed herein. System 100 shown in FIG. 1 is referenced in this example, although any other system described herein can utilize the process for acquiring object images. Referring to FIGS. 1 and 6, at block 600, controller CTR of system 100 can initiate the process and set variable i to 1. Variable i represents the iteration number of the process. At block 602, controller CTR can turn on x-ray sources XS corresponding to the $i^{th}$ pixels. Particularly, one or more x-ray sources XS can correspond to an $i^{th}$ group of x-ray sources. As described in further detail below, the process sequences through groups of i x-ray sources until the entirety of x-ray sources have been turned on and their x-ray beams XB detected.

At block 604, controller CTR can control x-ray detector XD to acquire the $i^{th}$ image. Particularly, x-ray detector XD can acquire the projection image of object O generated by the $i^{th}$ x-ray source(s). Controller CTR can determine whether acquisition of images from all i groups of x-ray sources has been completed (block 606). If it is determined that images have not been acquired from all i groups of x-ray sources, controller CTR can increment variable i by 1 (block 608) and the process can proceed to block 502 to acquire images from the remaining groups of x-ray sources.

If it is determined that images have been acquired from all i groups of x-ray sources, projection image reconstruction function PIRF can reconstruct tomography images of object O based on the projection images of the object (block 610). At block 612, a display of computer COM can display the reconstructed slice images of object O.

Figure 7:
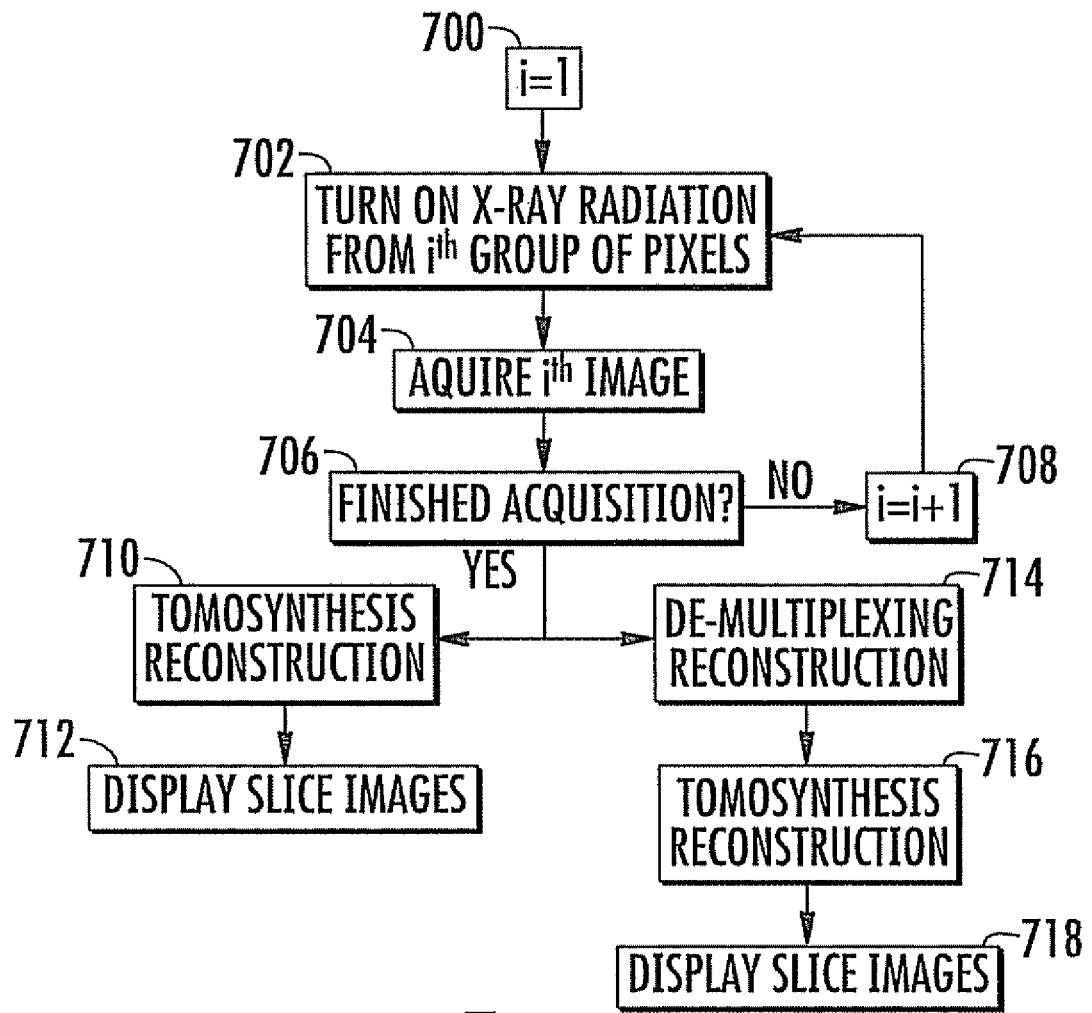
FIG. 7 is a flow chart of an exemplary process of multiplexing object images utilizing a MBFEX system according to an embodiment of the subject matter disclosed herein.

FIG. 7 is a flow chart illustrating an exemplary process of sequentially acquiring object images utilizing a MBFEX system according to an embodiment of the subject matter disclosed herein. System 100 shown in FIG. 1 is referenced in this example, although any other system described herein can utilize the process for acquiring object images. A LABVIEW™ (available from National Instruments Corporation) based software application can be utilized to generate a function for electronically controlling the triggering and switching of x-ray beam pixels and to synchronize the x-ray exposure with detector data collection.

Referring to FIGS. 1 and 7, at block 700, controller CTR of system 100 can initiate the process and set variable i to 1. Variable i represents the iteration number of the process. At block 702, controller CTR can turn on x-ray sources XS corresponding to the $i^{th}$ pixels. Particularly, one or more x-ray sources XS can correspond to an $i^{th}$ group of x-ray sources. As described in further detail below, the process sequences through groups of i x-ray sources until the entirety of x-ray sources have been turned on and their x-ray beams XB detected. In one embodiment, controller CTR can control the x-ray sources to generate multiplexed x-ray beams, which can be demultiplexed for image reconstruction as described below.

At block 704, controller CTR can control x-ray detector XD to acquire the $i^{th}$ image. Particularly, x-ray detector XD can acquire the projection image of object O generated by the $i^{th}$ x-ray source(s). Controller CTR can determine whether acquisition of images from all i groups of x-ray sources has been completed (block 706). If it is determined that images have not been acquired from all i groups of x-ray sources, controller CTR can increment variable i by 1 (block 708) and the process can proceed to block 702 to acquire images from the remaining groups of x-ray sources.

After image acquisition, projection image reconstruction function PIRF can apply tomosynthesis reconstruction (block 710) and display the reconstructed images via the display of computer COM (block 712). Alternatively, if the x-ray beams were multiplexed, projection image reconstruction function PIRF can demultiplex the images (block 714), apply tomosynthesis reconstruction (block 716) and display the reconstructed images via the display of computer COM (block 718).

Any suitable multiplexing imaging technique can be utilized in a system in accordance with the subject matter described herein. In this imaging mode, all or a sub-group of x-ray source pixels can be switched on simultaneously to illuminate the object. One example of a multiplexing technique includes a frequency division multiplexing. By using a multiplexing technique, the total image collection time can be significantly increased.

In one example of a multiplexing technique, an orthogonal frequency division multiplexing technique can be utilized. In this example, pulsed x-ray signals are generated and each x-ray beam can have a unique pulse width and repetition rate. Further, in this example, the detector records the transmitted x-ray intensity from the "on" x-ray pixels as a function of time. The recorded image is then de-multiplexed in the frequency domain to obtain the projection images from the individual pixels.

In another example of a multiplexing technique, a binary multiplexing technique can be utilized. An example of a binary multiplexing technique is described in U.S. patent application Ser. No. 11/804,897, titled "Methods, Systems, and Computer Program Products for Binary Multiplexing X-Ray Radiography, the disclosure of which is incorporated herein by reference in its entirety and which is commonly assigned to the same entities as the present patent application. In this example, a sub-set of the x-ray beams is switched on sequentially. The individual projection images are obtained by a linear combination of the composite images from the sub-sets.

Figure 8:
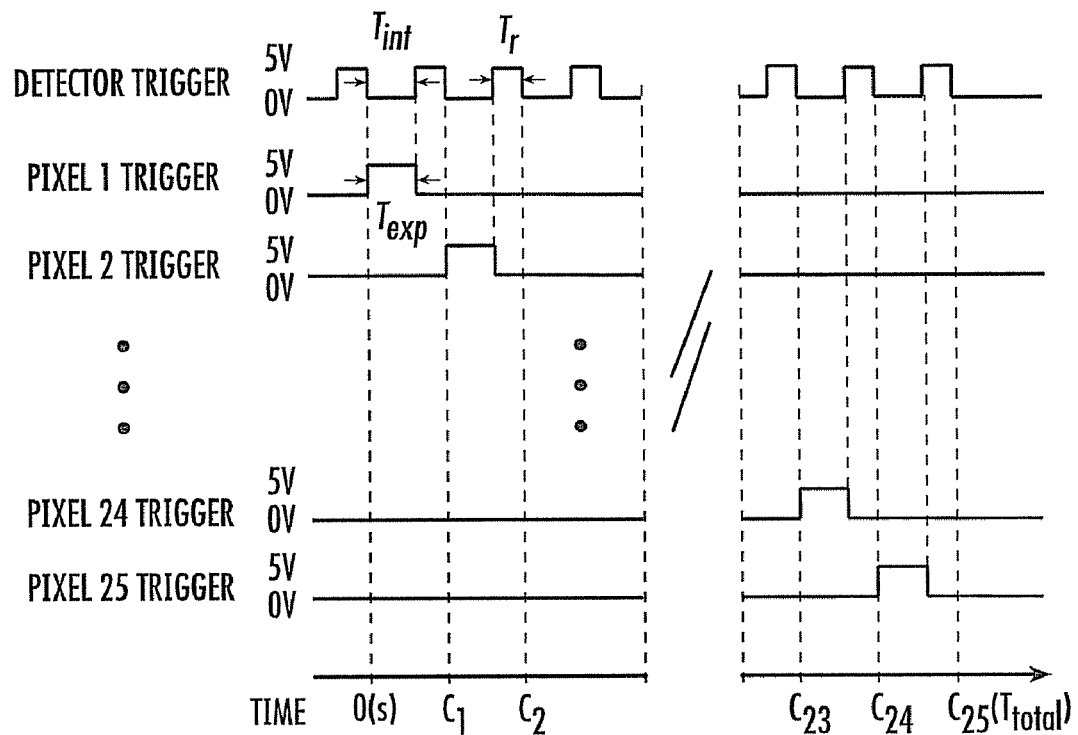
FIG. 8 is a timing diagram of a detector trigger and x-ray source pixel triggers according to an embodiment of the subject matter described herein.

X-ray sources may be triggered sequentially and projection images acquired accordingly. FIG. 8 is a timing diagram of a detector trigger and x-ray source pixel triggers according to an embodiment of the subject matter described herein. In this example, the system includes 25 x-ray source pixels. The signals represent control signals generated by a controller for controlling the x-ray sources and detector. X-ray radiation is on when a trigger signal is at 5 V. The exposure time is $T_{exp}$ for each pixel, which is the same as the integration time $T_{int}$ of the detector. The detector readout is triggered by the rising edge of the signal. The time to capture one image is represented by $T_r$. The total scan time is $25*(T_{exp}+T_r)$.

In accordance with the subject matter described herein, the field emission x-ray sources can each include a field emission cathode, a gate electrode that extracts electrons from the cathode when an electrical field is applied between the gate and the cathode, a focusing unit that focuses the field emitted electrons to a defined focal area on an anode, and the anode that produces the x-ray radiation when it is bombarded by the electron beam. The field emission cathode can includes carbon nanotubes, nanowires, and/or microfabricated tips. The gate electrodes can be either controlled individually or connected electrically.

Figure 9:
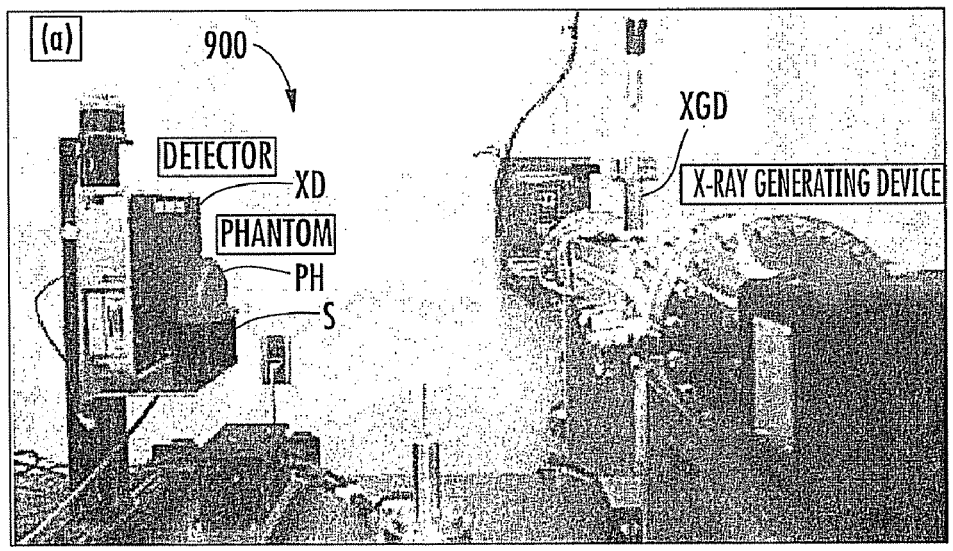
FIG. 9 is an image of a MBFEX system in accordance with the subject matter disclosed herein.

For purposes of experimentation, one embodiment of a system in accordance with the subject matter disclosed herein was constructed. FIG. 9 is an image of a MBFEX system generally designated 900 in accordance with the subject matter disclosed herein. Referring to FIG. 9, system 900 includes x-ray detector XD, x-ray generating device XGD, and a stage S for positioning of a phantom PH to be imaged. X-ray generating device XGD includes a carbon nanotube MBFEX source. X-ray detector XD is a flat panel x-ray detector. System 900 includes a control unit and a computer work station. X-ray detector XD can be a flat panel detector. The field of view can be about 19.5 cm×24.4 cm, which can ensure a full image of a breast. With a 127 μm pixel pitch, the total array size is 1536×1920. The detector can run under non-binning mode and 2×2 binning mode. Referring again to FIG. 7, in the user synchronization mode, the rising edge of a continuous TTL signal can trigger readout of the detector. The imaging time is determined by the integration window $T_{int}$ and the detector readout time $T_r$. $T_{int}$ is controllable through the triggering signal. X-ray radiation is delivered within the integration window $T_{int}$, and the radiation period is denoted as $T_{exp}$. The readout time $T_r$ depends on the acquisition mode. For the normal 2×2 binning modes, the readout time is 128 ms and 32 ms, respectively. In this example, the projection images are taken sequentially.

Figure 10:
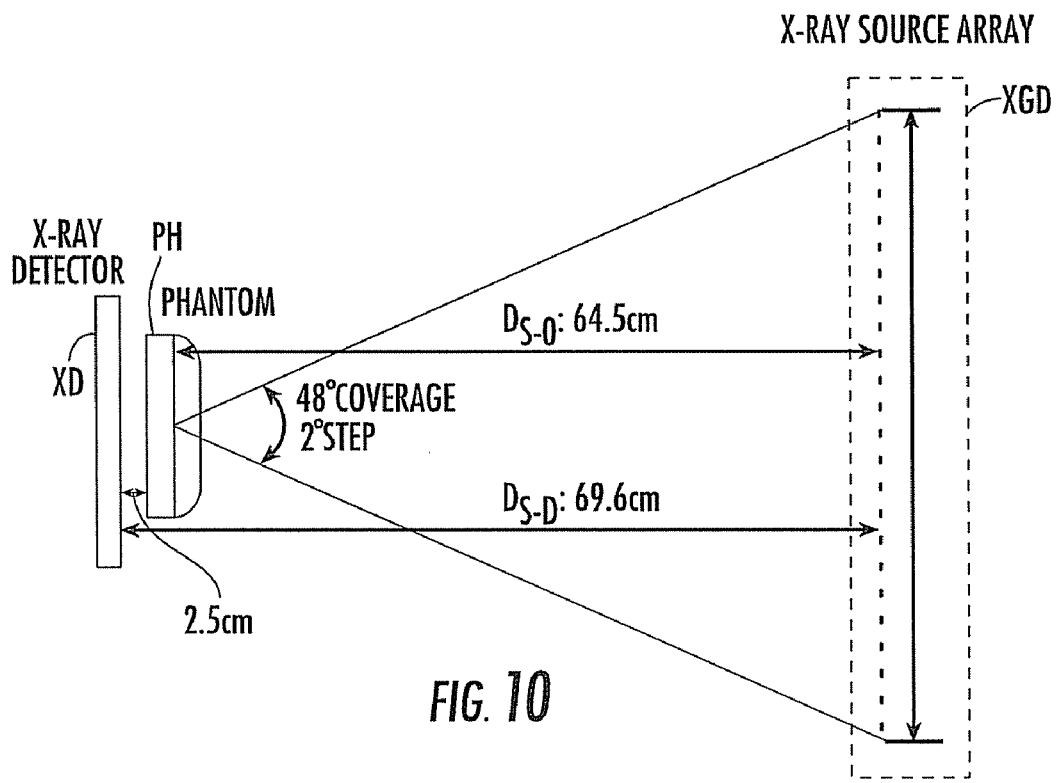
FIG. 10 is a schematic diagram showing the spatial relationship between an x-ray detector, a phantom, and x-ray sources of an x-ray generating device in accordance with the subject matter disclosed herein.

FIG. 10 is a schematic diagram showing the spatial relationship between x-ray detector XD, phantom PH, and x-ray sources XS of x-ray generating device XGD. The distance between the center of phantom PH and x-ray generating device XGD is about 64.5 cm. The x-ray generating device XGD to detector XD distance is about 69.6 cm, which leaves about a 2.5 cm air gap for a normal 5-cm breast phantom. The x-ray sources are arranged linearly to reduce the system complexity, with even-angular distribution and about a 2-degree step or increment. The total angular coverage of the x-ray generating device is about 48 degrees. In this system, the distance between the nearest x-ray focal spots varies from 2.5 cm to 2.7 cm, and the total span of the x-ray generating device array is about 57.5 cm.

Figure 11A:
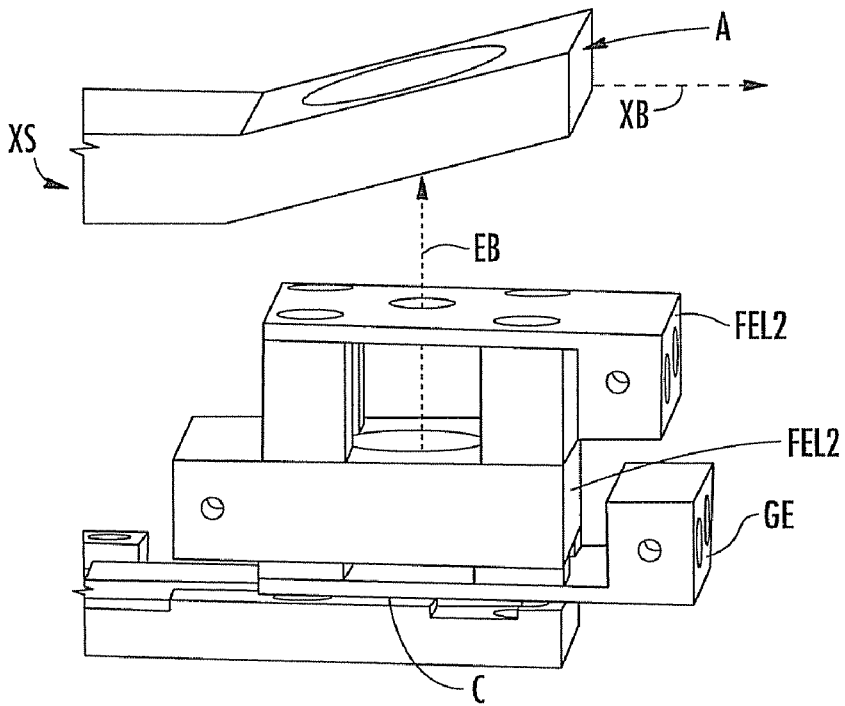
FIG. 11A is a perspective view of an x-ray source according to an embodiment of the subject matter disclosed herein.
Figure 11B:
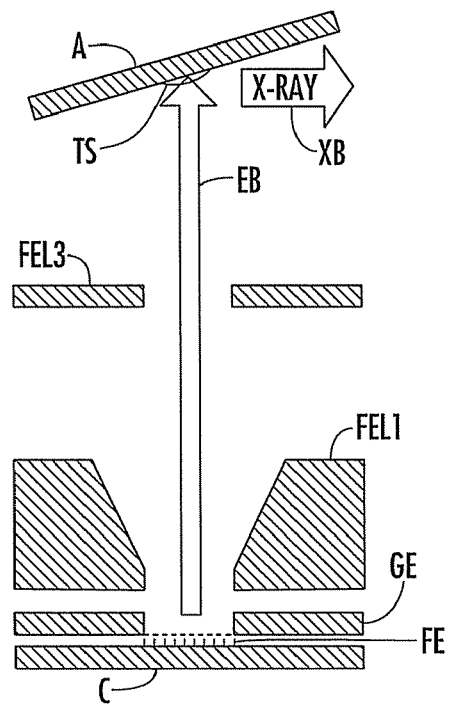
FIG. 11B is a schematic diagram of an x-ray source according to an embodiment of the subject matter disclosed herein.

System 900 includes a field emission x-ray source array. The construction of the 25 x-ray source pixels is substantially identical. FIGS. 11A and 11B are perspective and schematic diagram views, respectively, of an x-ray source XS according to an embodiment of the subject matter disclosed herein. Referring to FIGS. 11A and 11B, x-ray source XS can include an electron field emitter FE for emitting electrons. Electron field emitter FE can comprise one or more carbon nanotubes and/or other suitable electron field emission materials. Electron field emitter FE can be attached to a surface of a cathode C, conductive or contact line, or other suitable conductive material.

Electron field emitter FE can be controlled by a suitable controller (such as controller CTR shown in FIG. 4A) including MOSFET circuitry. The controller can control voltage sources to apply voltage between electron field emitter FE and a gate electrode GE to generate electric fields for extracting electrons from electron field emitter FE to thereby produce an electron beam EB. The controller can operate MOSFET circuitry for individually controlling electron beam emission by x-ray sources. The drains of the MOSFETs can be connected to cathode C for controlling electron beam emission by emitter FE. The MOSFETs can be turned on and off by the application of high signal (e.g., 5 V) and a low signal (e.g., 0 V) to the gates of the MOSFET. When a high signal is applied to the gate of a MOSFET, a drain-to-source channel of the transistor is turned on to apply a voltage difference between cathode C and gate electrode GE. A voltage difference exceeding a threshold can generate an electric field between cathode C and gate electrode GE such that electrons are extracted from electron field emitter FE. Conversely, when a low voltage (e.g., 0 V) is applied to the gate of a MOSFET, a drain-to-source channel is turned off such that the voltage at emitter FE is electrically floating and the voltage difference between cathode C and gate electrode GE cannot generate an electric field of sufficient strength to extract electrons from emitter FE.

Cathode C can be grounded, and other electrodes maintained at constant voltages during imaging acquisition. The gate voltage determines the x-ray tube current. Below a threshold, there is no current, and the current increases exponentially with gate voltage above the threshold. In one example, each x-ray pixel can provide a tube current of between 0.1 and 1 mA at 40 kVp. The controller is operable to apply voltage pulses of different frequencies to the gates of the MOSFET.

Further, x-ray source XS can include an anode A having a focus spot for bombardment by electron beam EB. A voltage difference can be applied between anode A and gate electrode GE such that a field is generated for accelerating electrons emitted by electron field emitter FE toward a target structure TS of anode A. The target structure can produce x-ray beams having a predetermined signal upon bombardment by electron beam EB. X-ray source XS can include focusing electrodes FEL1 and FEL2 for focusing electrons extracted from electron field emitter FE on target structure TS and thus reduce the size of electron beam EB. Focusing electrodes FEL1 and FEL2 can be controlled by application of voltages to the focusing electrodes by a voltage source. The voltage applied to the focusing electrodes controls the electron trajectory. The gate voltage can be varied depending on required flux.

Electron field emitter FE and gate electrode GE can be contained within a vacuum chamber with a sealed interior at about $10^{-7}$ Torr pressure. The interior of the vacuum chamber can be evacuated to achieve a desired interior pressure. X-ray radiation can travel from the interior of the vacuum chamber to its exterior through an x-ray permeable portion or window. In one example, the x-ray permeable portion or window can be a beryllium (Be) or molybdenum (Mo) window. The molybdenum anode and filter combination can be used for breast imaging among other applications. Up to a 40 keV high voltage can be applied on anode A. Anode A can be suitably shaped and/or angled such that the generated x-ray beams are transmitted toward an object from a plurality of different viewing angles. The targeted performance for the source is that each x-ray source pixel can provide a 10 mA peak current at 200 μm×200 μm effective focal spot size. Alternatively, the energy filter can comprise Cerium, and the voltage applied on anode A can be in the range of 60-80 kV.

Figure 12:
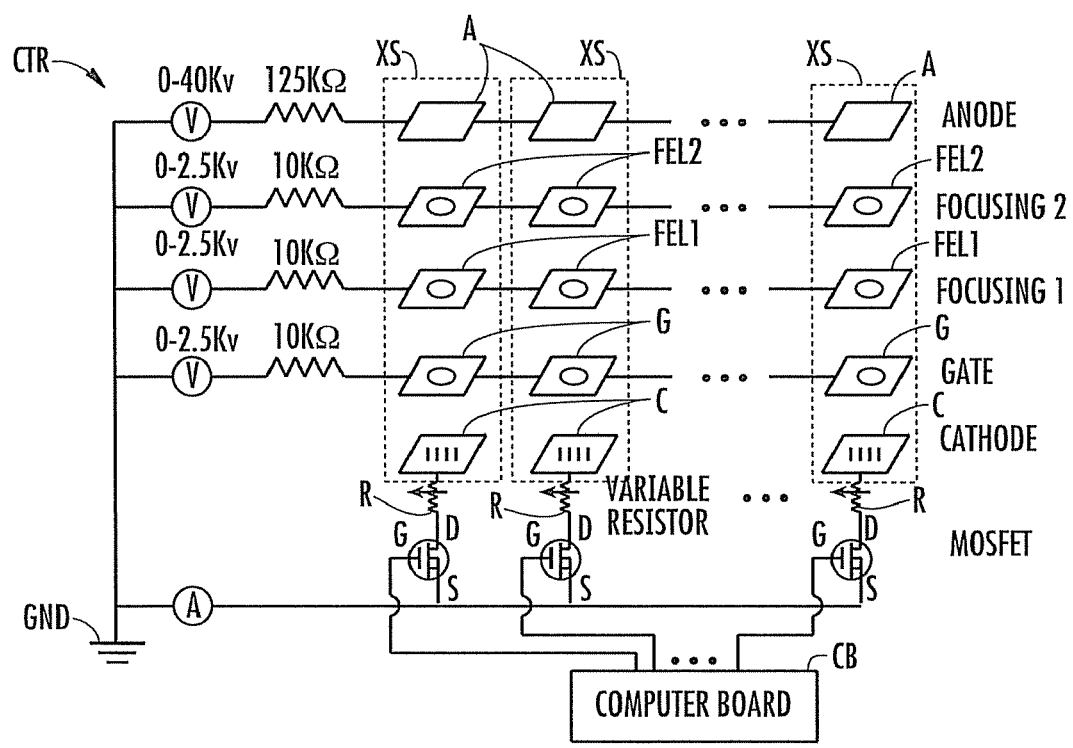
FIG. 12 is a circuit diagram of a controller configured to control the emission of x-ray beams from a plurality of x-ray sources in accordance with the subject matter described herein.

FIG. 12 is a circuit diagram of controller CTR configured to control the emission of x-ray beams from a plurality of x-ray sources in accordance with the subject matter described herein. Referring to FIG. 12, controller CTR can include a plurality of MOSFETs operable to individually switch on and off x-ray sources XS. The drains (D), gates (G), and sources (S) of the MOSFETs are connected to respective cathodes C, TTL trigger signals generated by a computer board CB, and a common ground GND. When a TTL trigger signal is at a low state, the conduction channel between the source and drain is closed. This causes the carbon nanotube cathode potential to float relatively to the common ground GND, and no electrons are emitted from cathode C and thus no x-ray beams are generated. When the TTL trigger signal is at a high state, cathode C is grounded because of the opened conduction channel. As a result, electrons are extracted by the electrical field between gate G and cathode C, and x-ray radiation is produced. The delay time (between switching of the TTL signal and the conduction channel) of the MOSFET is about 35 to 45 ns, which is sufficient considering the tens of milliseconds x-ray exposure period. The x-ray source pixels can be switched individually at any given time during the imaging acquisition process, which provides great flexibility. Variable resistors R are built-in for compensation of the variations in the individual cathode performance.

Figure 13:
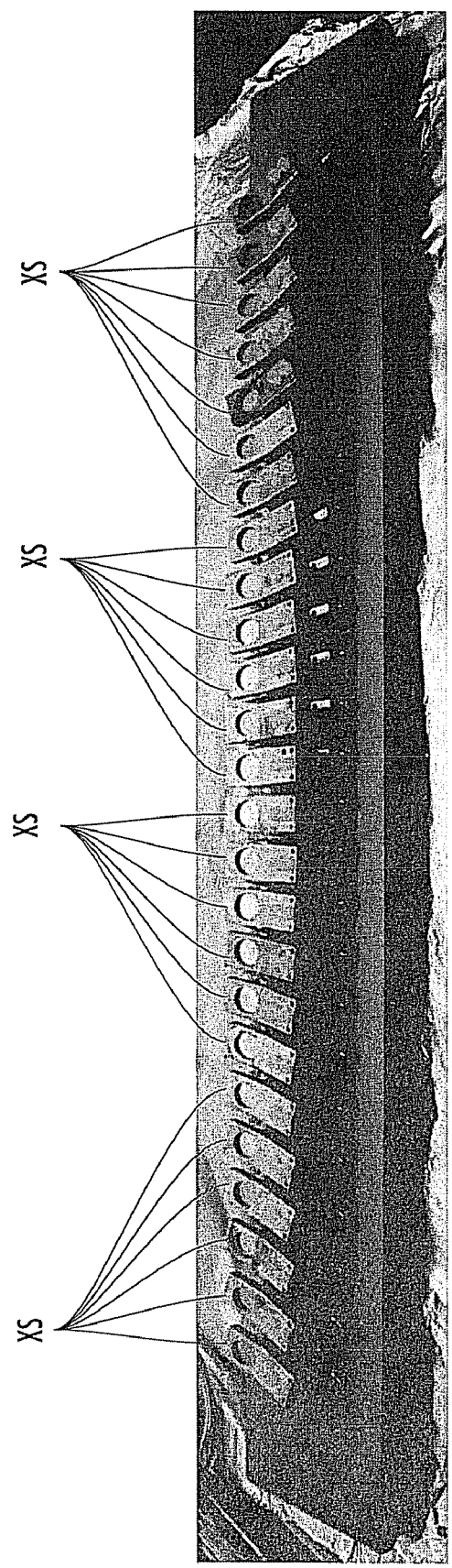
FIG. 13 is an image of a MBFEX x-ray source array according to an embodiment of the subject matter described herein.

FIG. 13 is an image of a MBFEX x-ray source array according to an embodiment of the subject matter described herein. The array includes 25 individually controllable x-ray source pixels XS which are tilted towards the iso-center of a position for placement of an object to be imaged.

To reconstruct slice images, an iterative ordered-subset convex (OSC) technique can be used by the reconstruction function based on a maximum-likelihood model. The reconstruction technique applies a sharing method to convert all projections images to a common frame of reference, and then uses a pre-computed cone-beam model to project and back-project in the common frame. To reduce the computation load, non-cubic voxels are reconstructed. This technique has been verified on both simulated data and breast phantom images measured from a field emission x-ray source array with a limited number of pixels.

Table 1 shows a comparison of system 900 shown in FIG. 9 with commercially available systems.

TABLE 1

System Comparison

|  | System 900 of FIG. 9 | GE: Senographe 2000D | Siemens: Mammomat Novation | Hologic: Selenia |
|---|---|---|---|---|
| X-Ray kVp, mA | 25-35 kVp, 10 mA | 25-30 kVp, ~130 mA | ~28 kVp, ~180 mA | 24-39 kVp, ~100 mA |
| Focal Spot Size | 200 µm | 300 µm | 300 µm + blur* | 300 µm + blur* |
| Target/Filer | Mo/Mo | Mo/Mo, Rh/Rh | W/Rh | (Mo, W)/(Rh, Al) |
| Angle Coverage | 48 degrees | 50 degrees | 50 degrees | 30 degrees |
| View Numbers | 25 | 11 | 25/49 | 11 |
| Gantry Motion | Stationary | Step and Shoot | Continuous Rotation | Continuous Rotation |
| Flat-Panel Detector | A-silicon | Cs: I a-silicon | Direct converter a-selenium | Direct converter a-selenium |
| Detector Size | 19.5 × 24.4 cm pixel pitch: 127 µm | 18.00 × 23.04 pixel pitch: 100 µm | 23.9 × 30.5 cm pixel pitch: 85 µm | 24 × 29 cm pixel pitch: 70 µm (140 µm for DBT) |
| Readout Time | 0.128 s/ 0.032 s | 0.3 s | 0.6 s/0.3 s | 0.6 s |
| Integration Time | 0.32 s | 0.4 s | 0.2 s | 1.0 s |
| Exposure Time | 0.32 s | ~0.1 s | ~0.03 s | 0.073 s |
| Total Scan Time** | 11.2 s for 25 views | 7 s for 11 views | 20 s/39.2 s for 25/49 views | 18 s for 11 views |
| Reconstruction Technique | Ordered subsets convex (maximum likelihood) | ML-EM | FBP: filtered back projection | FBP: filtered back projection |

*Additional focal spot blur due to the gantry movement during exposure
**Total scan time = (view number) × (cycle time); cycle time = (readout time) + (integration time)

Advantages of a system in accordance with the subject matter disclosed herein over commercially available systems include: (1) the total spot size of system 900 is 200 µm while the values of other systems are 300 µm or larger; (2) the stationary design provides less gantry vibration by eliminating the mechanical movement; and (3) the exposure time matches the detector integration window. The targeted total scan time (8.8 s in binning mode and 11.2 s in full-resolution mode, 25 viewing angles) is shorter, which can be further reduced by increasing the x-ray tube current which requires relaxing of the focal spot size.

Figure 14:
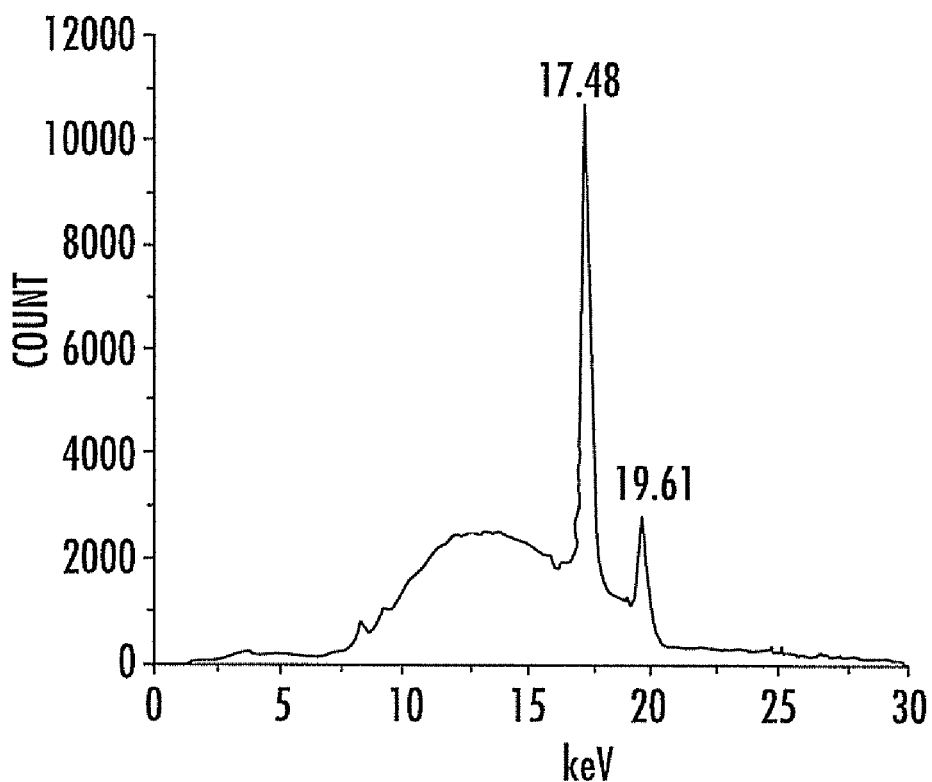
FIG. 14 is a graph of an experimentally measured energy spectrum of the system shown in FIG. 9.

The energy spectrum of the x-ray source of system 900 was measured at 28 keV using a Si-pin photodiode detector. The energy filters used can be selected such that the x-ray radiation from each of the x-ray focal spots have the same energy spectrum. The spectrum is consistent when measured at different locations within the field of view and from different x-ray source pixels. The experimentally measured energy spectrum of system 900 (FIG. 9) at 28 keV is shown in the graph of FIG. 14. The results shown in FIG. 14 agree well with a typically Mo/Mo x-ray spectrum. Two molybdenum characteristic peaks, one at 17.5 keV and the other at 19.6 keV, can be recognized in the graph. Alternatively, the energy filters can be varied such that energy spectra from the x-ray focal spots can be individually controlled.

Figure 15:
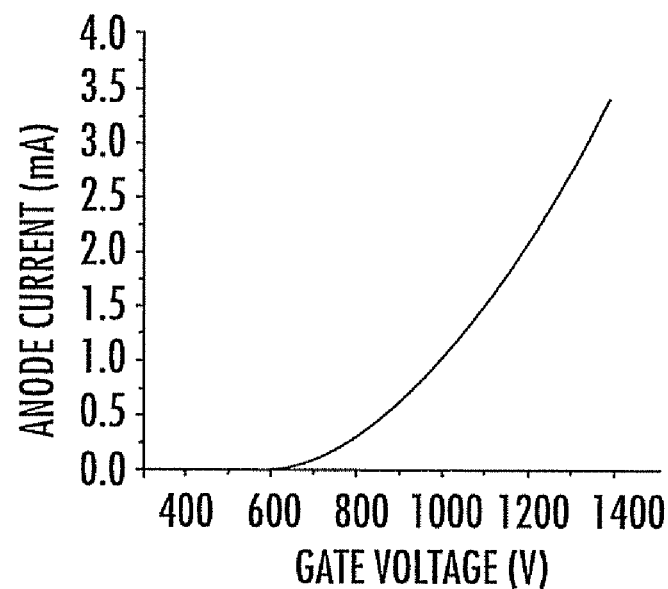
FIG. 15 is a graph of anode current as a function of gate voltage for the system shown in FIG. 9.

FIG. 15 is a graph of anode current as a function of gate voltage for system 900 shown in FIG. 9. The threshold value for this x-ray source is about 650 V. The emission current from the carbon nanotube cathode depends on the electrical field between the gate and the cathode following the Fowler-Nordheim equation. In this particular x-ray source, 72% of the total current passes through the gate electrode and reaches the anode to produce x-ray radiation (also denoted as anode current). The graph of FIG. 15 shows the typical anode current versus gate voltage data measured from one pixel. Due to the voltage limitation of the electronic control devices, the maximum gate voltage that can be applied in this experiment is 1500 V, which limits the anode current to ~4 mA, below the targeted value of 10 mA. This limitation can be overcome by changing the design and/or optimizing the carbon nanotube cathode (when measured in a separate setup, the cathodes fabricated under the same conditions can produce over 10 mA consistently at higher gate voltages).

In this experiment, nine of the pixels of system 900 shown in FIG. 9 have been characterized. Due to the variation in the carbon nanotube cathodes, the gate voltages required to obtain the same current are different. As a reference, the voltages vary from 925 V to 1465 V for 1 mA tube current. Table 2 shows the gate voltage and standard deviation of current for the nine pixels as obtained by this experiment.

TABLE 2

Gate Voltage and Standard Deviation of Pixels

| X-Ray Source Number | Gate Voltage (V) | Standard Deviation of Current (mA) |
|---|---|---|
| 1 | 1230 | 0.02 |
| 2 | 925 | 0.01 |

TABLE 2-continued

Gate Voltage and Standard Deviation of Pixels

| X-Ray Source Number | Gate Voltage (V) | Standard Deviation of Current (mA) |
|---|---|---|
| 3 | 1230 | 0.02 |
| 4 | 1015 | 0.01 |
| 5 | 1300 | 0.03 |
| 6 | 1070 | 0.01 |
| 7 | 1160 | 0.01 |
| 8 | 1465 | 0.02 |
| 9 | 1030 | 0.01 |

The voltage difference can be compensated by the variable resistors in the controller. With the improvement of fabrication technique and cathode quality control, the variation can be reduced. The current stability was determined by measuring the current of 100 pulsed x-rays at constant voltage. The standard deviation of the current is less than 0.03 mA for all pixels tested.

Figure 16:
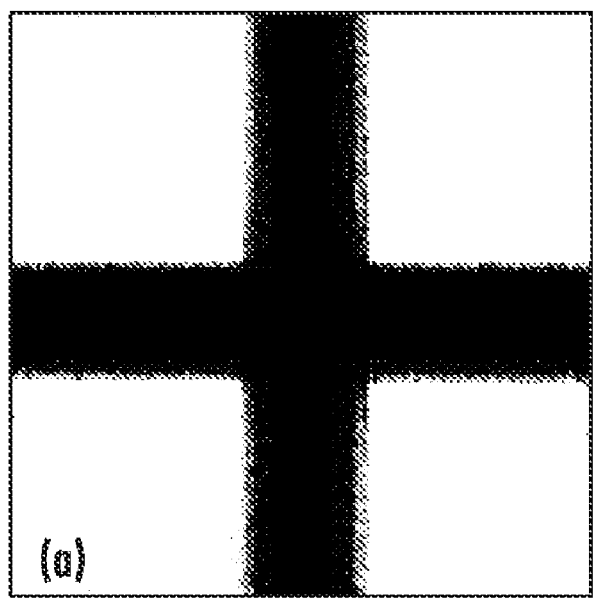
FIG. 16 is a projection image of a cross phantom obtained in accordance with the subject matter described herein.
Figure 17:
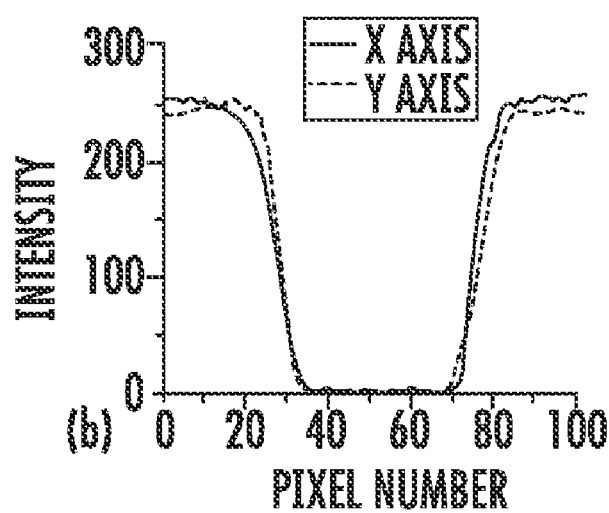
FIG. 17 is a graph showing the line profiles of the two wires obtained in accordance with the subject matter described herein.

In this experiment, the designed x-ray focal spot size is about 200×200 μm for all 25 x-ray sources. The actual values were measured following the European standard EN12543-5. A customized cross wire phantom made of 1 mm tungsten wire was fabricated to measure the focal spot size along two orthogonal directions simultaneously. The phantom was placed close to the x-ray source to obtain the large magnification factor. The voltages applied to the two focusing electrodes were first varied to optimize the focal spot size. It was found that the optimal focal spot size is achieved when the two focusing electrodes are at 500 V and 1600 V, respectively. A typical projection image of the cross phantom is shown in FIG. 16. FIG. 17 is a graph showing the line profiles of the two wires, where the X axis is the direction of the x-ray source array, and the Y axis is perpendicular to the array.

Table 3 shows the focal spot size measurement of the nine x-ray source pixels.

TABLE 3

Focal Spot Size Measurement of Pixels

| X-Ray Source Number | $F_x$: Parallel to X-Ray Source Array | $F_y$: Perpendicular to X-Ray Source Array |
|---|---|---|
| 1 | 0.20 mm | 0.20 mm |
| 2 | 0.20 mm | 0.17 mm |
| 3 | 0.18 mm | 0.19 mm |
| 4 | 0.19 mm | 0.19 mm |
| 5 | 0.20 mm | 0.19 mm |
| 6 | 0.19 mm | 0.17 mm |
| 7 | 0.18 mm | 0.17 mm |
| 8 | 0.19 mm | 0.19 mm |
| 9 | 0.18 mm | 0.19 mm |

The results shown in Table 3 agree well with the designed specification of 0.20×0.20 mm. The x-ray sources have an isotropic focal spot with an average value of 0.19 mm. Measurements from different x-ray sources are also consistent.

Tomosynthesis reconstruction requires precise system geometry parameters. An analytic method was applied based on identification of ellipse parameters for the geometry calibration, which was first established for cone-beam CT calibration. A phantom with two point objects with known distance was machined. The geometry parameters of the 25 x-ray sources were individually calibrated. Six projection images of the phantom (60-degree rotation in-between) were acquired for each pixel. The traces of the two balls form two ellipses on the detector plane. The parameters, including the source-to-detector distance and x-ray source offset values on the detector plane, can be further calculated based on these elliptical curves. The source-to-detector distance is calculated to be 69.3 cm with 2 mm uncertainty. The distances between the x-ray sources are also calculated. The results agree with the design values within 1 mm uncertainty.

In one embodiment, an anti-scattering component can be positioned between the x-ray detector and the location for positioning the object. In particular, one-dimensional or two-dimensional anti-scattering grids can be made to utilize the advantage of linear MBFEX. For instance, in the case of a two-dimensional grid, the anti-scattering component can be adjusted based on a position of one or more of the x-ray sources being activated. Alternatively, in the case of a one-dimensional anti-scattering grid, the grid lines can run in either parallel or perpendicular to the linear/arc direction of the MBFEX. The grid geometry can be tailored to enable fan-beam reconstruction to enhance the tomographic image quality and increase the reconstruction speed.

Using such an anti-scattering component, a cone beam x-ray source can be used to produce fan-beam reconstructed tomography images of an object. For example, referring again to FIG. 4A, a plurality of stationary field emission x-ray sources XS can be provided. X-ray sources XS can be spatially distributed in a substantially linear array (e.g., x-ray generating device XGD). The object O can then be irradiated with x-ray cone beams produced by x-ray sources XS to generate two-dimensional projection images of object O. A linear anti-scattering grid AS can be placed between object O and detector XD to reduce scatter of the x-ray cone beams. Two-dimensional projection images of object O can be detected, and the two-dimensional projection images can be divided into groups of one-dimensional data. These groups of one-dimensional data can be collected from all of the different x-ray sources XS, and a fan beam reconstruction can be used to reconstruct slice images of object O from the groups of one-dimensional data. The slice images can be merged together to form a three-dimensional image of object O.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A stationary x-ray digital breast tomosynthesis system comprising:
    an field emission x-ray source that generates x-ray radiation from an array of spatially distributed x-ray focal spots configured to image a human breast from different viewing angles by electronically activating a corresponding array of spatially distributed field emission cathodes;
    an area x-ray detector configured to detect the projection images of the breast;
    an electronic controller for activating the x-ray radiation from the different x-ray focal spots in the x-ray source in a sequence and for synchronizing x-ray exposure from a given focal spot with image collection by the x-ray detector; and
    wherein tomography images of the breast are reconstructed using a plurality of projection images of the breast collected from different viewing angles without moving any of the x-ray source, the breast, or the x-ray detector.

2. The x-ray digital breast tomosynthesis system of claim 1, wherein the x-ray source includes a plurality of focal spots arranged in a substantially straight line parallel to an imaging plane of the x-ray detector.

3. The x-ray digital breast tomosynthesis system of claim 1, wherein the x-ray source includes a plurality of focal spots arranged substantially along an arc, wherein the focal spots define a plane that is substantially perpendicular to an imaging plane of the x-ray detector, wherein all the x-ray focal spots are equal distance to an iso-center.

4. The x-ray digital breast tomosynthesis system of claim 1, wherein the x-ray source includes a plurality of focal spots arranged in a two-dimensional matrix on an x-ray anode.

5. The x-ray digital breast tomosynthesis system of claim 1, wherein the x-ray source includes focal spots of substantially the same size.

6. The x-ray digital breast tomosynthesis system of claim 1, wherein the x-ray source includes focal spots having sizes ranging between about 0.05 mm and about 2 mm.

7. The x-ray digital breast tomosynthesis system of claim 1, wherein the x-ray source is configured to generate cone-shaped x-ray beams, and wherein central axes of the x-ray beams are substantially directed towards an iso-center.

8. The x-ray digital breast tomosynthesis system of claim 1, further comprising an electronic circuit to individually control the x-ray intensities from the different x-ray focal spots such that they can either be the same or be modulated to deliver a desired intensity or intensity distribution on the breast to be imaged.

9. The x-ray digital breast tomosynthesis system of claim 1, wherein the array of spatially distributed x-ray focal spots in the x-ray source comprises between about 10 and 100 x-ray focal spots covering viewing angles of between 10° and 100° degrees.

10. The x-ray digital breast tomosynthesis system of claim 1, comprising a plurality of individually controllable electron field emission cathodes, one or more x-ray anodes, and an electron focusing lens that focuses the electron beam from a cathode to a desired area on an x-ray anode.

11. The x-ray digital breast tomosynthesis system of claim 10, wherein the electron focusing lens is a modified Einzel type lens with a plurality of electrostatic focusing electrodes.

12. The x-ray digital breast tomosynthesis system of claim 10, wherein the electron field emission cathodes include at least one of the following: nanowires, nanotubes, and carbon nanotubes.

13. The x-ray digital breast tomosynthesis system of claim 1, comprising a controller configured to adjust focal spot sizes of different x-ray beams.

14. The x-ray digital breast tomosynthesis system of claim 1, comprising a controller including a field-effect-transistor based electronic circuit configured to activate the x-ray sources.

15. The x-ray digital breast tomosynthesis system of claim 1, comprising an anti-scattering component positioned between the x-ray detector and the location for positioning the breast.

16. The x-ray digital breast tomosynthesis system of claim 15, wherein the anti-scattering component is adjustable based on a position of one or more of the x-ray sources being activated.

17. The x-ray digital breast tomosynthesis system of claim 1, wherein the x-ray source comprises x-ray anodes configured at different voltages to produce x-ray radiation with two energies.

18. The x-ray digital breast tomosynthesis system of claim 17, wherein the x-ray source comprises 12 anodes configured at low voltage and 13 anodes configured at high voltage to enable the system for dual-energy imaging.

19. The electronic circuit of claim 8, further comprising an array of variable resistors which are calibrated to compensate for variations in the performance of the cathodes.

20. A stationary x-ray digital breast tomosynthesis system configured to image a human breast from different viewing angles for reconstruction without moving any of the source, the breast, or the detector, the system comprising:
  a field emission x-ray source that generates x-ray radiation from an array of x-ray focal spots that are spatially distributed in a substantially straight line parallel to the imaging plane of the x-ray detector by electronically activating a corresponding array of spatially distributed field emission cathodes;
  an area x-ray detector configured to detect the projection images of the breast;
  an electronic controller for sequentially activating the x-ray radiation from the different x-ray focal spots and varying the intensity of the x-ray radiation based on the distance between the x-ray focal spot and the object breast to be imaged such that the x-ray dose delivered to the breast from every viewing angle is substantially the same; and
  wherein tomography images of the breast are reconstructed using a plurality of projection images of the breast collected from different viewing angles.

21. The x-ray digital breast tomosynthesis system of claim 20, wherein the x-ray source is configured to generate cone-shaped x-ray beams, and wherein a central axis of each of the x-ray beams is substantially directed towards an iso-center.

22. The x-ray digital breast tomosynthesis system of claim 20, wherein adjacent focal spots of the x-ray source have substantially the same angular spacing with respect to an iso-center.

23. The x-ray digital breast tomosynthesis system of claim 20, wherein the adjacent focal spots of the x-ray source have substantially the same linear spacing.

24. A stationary x-ray digital breast tomosynthesis system configured to image a human breast from different viewing angles for reconstruction without moving any of the source, the breast, or the detector, the system comprising:
  a field emission x-ray source that generates x-ray radiation from an array of x-ray focal spots that are spatially distributed along an arc substantially perpendicular to an imaging plane of the x-ray detector, wherein the focal spots are equal distance to the breast to be imaged by electronically activating a corresponding array of spatially distributed field emission cathodes;
  an area x-ray detector configured to detect the projection images of the breast;
  an electronic controller for sequentially activating the x-ray beam from the different x-ray focal spots and delivering the same x-ray tube current to each focal spot; and
  wherein tomography images of the breast are reconstructed using a plurality of projection images of the breast collected from different viewing angles.

25. A quasi-monochromatic x-ray digital breast tomosynthesis system configured to image a human breast, the system comprising:
  an x-ray source that generates scanning cone-beam x-ray radiation from an array of spatially distributed x-ray focal spots;
  one or more energy filters positioned between the x-ray source and an object to be, imaged;

an x-ray detector configured to collect projection images of the object;

an electronic control circuit that allows imaging of the object by simultaneously activating a plurality of x-ray beams at a given time based on a multiplexing imaging scheme, and synchronizes x-ray exposure with data collection by the x-ray detector; and a computer in communication with the electronic control circuit for de-multiplexing the projection images;

wherein tomography images of the object are reconstructed using a plurality of projection images of the object collected from different viewing angles.

26. The x-ray digital breast tomosynthesis system of claim 25, wherein the one or more energy filters comprise a plurality of energy filters that are the same such that the x-ray radiations from each focal spots have substantially the same energy spectrum.

27. The device of claim 25, wherein the one or more energy filters comprise a plurality of energy filters that are varied such that energy spectra from the x-ray focal spots are individually controlled.

28. The x-ray digital breast tomosynthesis system of claim 25, wherein the projection images are collected by the binary multiplexing scheme.

29. The x-ray digital breast tomosynthesis system of claim 25, wherein the projection images are collected by the frequency division multiplexing scheme.

30. The x-ray digital breast tomosynthesis system of claim 25, wherein the energy filter comprises Cerium and wherein the x-ray source comprises an x-ray anode that operates on a voltage in the range of 60-80 kV.

31. The x-ray digital breast tomosynthesis system of claim 25, wherein the projection images from the different viewing angles are generated by electronically switching the x-ray beams from different focal spots without moving any of the x-ray source, the detector, or the patient.

32. A x-ray digital tomosynthesis system comprising:

a field emission x-ray source that generates a scanning x-ray beam from an array of spatially distributed x-ray focal spots configured to image an object from different viewing angles for tomosynthesis reconstruction;

an array of energy filters positioned between the x-ray source and the object such that each of energy filters in the array filters the x-ray radiation from a corresponding x-ray focal spot;

an area x-ray detector configured to detect projection images of the object;

an electronic controller for activating the x-ray beam from different x-ray focal spots in a sequence, either one beam or a plurality of the beams simultaneously, and for synchronizing x-ray exposure with image collection by the x-ray detector; and wherein tomography images of the object are reconstructed using a plurality of projection images of the object from different viewing angles.

33. The system of claim 32 wherein a dual energy tomosynthesis scan is generated without changing a voltage applied to the field emission x-ray source by varying the energy filters used for each of the x-ray focal spots.

34. A multiplexing x-ray digital tomosynthesis system comprising:

a field emission x-ray source for generating a scanning x-ray beam from an array of spatially distributed x-ray focal spots configured to image an object from different viewing angles for tomosynthesis reconstruction;

an energy filter positioned between the x-ray source and the object;

an area x-ray detector configured to detect the projection images;

an electronic controller for imaging of the object by simultaneously activating a plurality of the x-ray beams at a given time based on a multiplexing imaging scheme, and for synchronizing x-ray exposure with data collection by the x-ray detector;

wherein the projection images are de-multiplexed; and wherein tomography images of the object are reconstructed using a plurality of projection images of the object from different viewing angles.

35. The x-ray digital tomosynthesis system of claim 34, further comprising a controller for varying the x-ray intensity from each focal spot by controlling the field emission current from a field emission cathode and adjusting the focal spot size by varying the voltage applied to an electron focusing lenses.

36. A method of producing tomography images of an object, the method comprising:

providing a plurality of stationary field emission x-ray sources spatially distributed with respect to an object to be imaged;

generating a plurality of x-ray beams from the plurality of stationary field emission x-ray sources;

filtering the x-ray beams produced by the x-ray sources to generate at least one of monochromatic or quasi-monochromatic x-ray beams;

irradiating the object with the monochromatic or quasi-monochromatic x-ray beams to generate projection images of the object;

detecting the projection images of the object; and reconstructing tomography images of the object based on the projection images of the object.

37. The method of claim 36, wherein the x-ray sources include a plurality of focal spots arranged in a substantially straight line parallel to an imaging plane of the x-ray detector.

38. The method of claim 36, wherein the x-ray sources include a plurality of focal spots arranged substantially along an arc, wherein the focal spots define a plane that is substantially perpendicular to an imaging plane of the x-ray detector.

39. The method of claim 36, wherein the x-ray sources include a plurality of focal spots arranged in a two-dimensional matrix on an anode.

40. A method of producing images of an object using at least one of monochromatic and quasi-monochromatic x-ray beams, the method comprising:

providing a plurality of stationary field emission x-ray sources spatially distributed with respect to an object to be imaged;

irradiating the object with at least one of monochromatic and quasi-monochromatic x-ray beams produced by the x-ray sources to generate projection images of the object;

detecting the projection images of the object; and reconstructing displayable images of the object based on the projection images of the object.

41. The method of claim 40, wherein the x-ray sources include a plurality of focal spots arranged in a substantially straight line parallel to an imaging plane of the x-ray detector.

42. The method of claim 40, wherein the x-ray sources include a plurality of focal spots arranged substantially along an arc, wherein the focal spots define a plane that is substantially perpendicular to an imaging plane of the x-ray detector.

43. The method of claim 40, wherein the x-ray sources include a plurality of focal spots arranged in a two-dimensional matrix on an anode.

44. The method of claim 40, wherein the x-ray sources include a plurality of individually controllable electron field emission cathodes and one or more x-ray anodes.

45. The method of claim 44, wherein the electron field emission cathodes include at least one of the following: nanowires, nanotubes, and carbon nanotubes.

46. A method of producing fan-beam reconstructed tomography images of an object using a cone beam x-ray source, the method comprising:

provitding a plurality of stationary field emission x-ray sources spatially distributed in a substantially linear array;

irradiating the object with at least one of monochromatic or quasi-monochromatic x-ray cone beams produced by the x-ray sources to generate two-dimensional projection images of the object;

placing a linear anti-scattering grid between the object and the detector to reduce scatter of the x-ray cone beams;

detecting the two-dimensional projection images of the object;

dividing the two-dimensional projection images into groups of one-dimensional data;

reconstructing slice images of the object from the groups of one-dimensional data; and merging the slice images of the object to form a three-dimensional image of the object.

* * * * *

UNITED STATES PATENT AND TRADEMARK OFFICE
CERTIFICATE OF CORRECTION

PATENT NO. : 7,751,528 B2  
APPLICATION NO. : 12/176056  
DATED : July 6, 2010  
INVENTOR(S) : Zhou et al.

Page 1 of 1

It is certified that error appears in the above-identified patent and that said Letters Patent is hereby corrected as shown below:

At Column 1, Line 14 under the heading "GOVERNMENT INTEREST"

Please delete the following paragraph:

"This presently disclosed subject matter was made with U.S. Government support under Grant No. US4CA119343 awarded by the National Cancer Institute. Thus, the U.S. Government has certain rights in the presently disclosed subject matter."

And replace it with the following paragraph:

-- This invention was made with government support under Grant Nos. U54 CA119343 awarded by the National Cancer Institute. The government has certain rights in the invention. --

Signed and Sealed this  
Twenty-ninth Day of May, 2012

David J. Kappos  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,751,528 B2 | Page 1 of 1 |
| APPLICATION NO. | : 12/176056 | |
| DATED | : July 6, 2010 | |
| INVENTOR(S) | : Zhou et al. | |

It is certified that error appears in the above-identified patent and that said Letters Patent is hereby corrected as shown below:

At Column 1, Line 14 under the heading "GOVERNMENT INTEREST"

Please delete the following paragraph:

"This presently disclosed subject matter was made with U.S. Government support under Grant No. US4CA119343 awarded by the National Cancer Institute. Thus, the U.S. Government has certain rights in the presently disclosed subject matter."

And replace it with the following paragraph:

-- This invention was made with government support under U54 CA119343 awarded by NIH. The government has certain rights in the invention. --

This certificate supersedes the Certificate of Correction issued May 29, 2012.

Signed and Sealed this
Twenty-fifth Day of September, 2012

David J. Kappos
*Director of the United States Patent and Trademark Office*